United States Patent
Kawaura et al.

(10) Patent No.: US 11,337,700 B2
(45) Date of Patent: May 24, 2022

(54) SUBCUTANEOUS TISSUE DEVICE

(71) Applicant: TERUMO KABUSHIKI KAISHA, Tokyo (JP)

(72) Inventors: Masakatsu Kawaura, Sunnyvale, CA (US); Shuji Uemura, San Francisco, CA (US); David Batten, San Francisco, CA (US)

(73) Assignee: TERUMO KABUSHIKI KAISHA, Tokyo (JP)

(*) Notice: Subject to any disclaimer, the term of this patent is extended or adjusted under 35 U.S.C. 154(b) by 64 days.

(21) Appl. No.: 16/621,427

(22) PCT Filed: Jun. 5, 2018

(86) PCT No.: PCT/JP2018/021621
§ 371 (c)(1),
(2) Date: Dec. 11, 2019

(87) PCT Pub. No.: WO2018/230402
PCT Pub. Date: Dec. 20, 2018

(65) Prior Publication Data
US 2020/0205828 A1     Jul. 2, 2020

Related U.S. Application Data

(60) Provisional application No. 62/518,289, filed on Jun. 12, 2017, provisional application No. 62/518,179, (Continued)

(51) Int. Cl.
*A61B 17/08*     (2006.01)
*A61B 17/04*     (2006.01)
(Continued)

(52) U.S. Cl.
CPC .......... *A61B 17/08* (2013.01); *A61B 17/0482* (2013.01); *A61B 17/06066* (2013.01);
(Continued)

(58) Field of Classification Search
CPC .................. A61B 17/08; A61B 17/12; A61B 2017/00668; A61B 2017/0641; A61B 2017/081; A61B 2017/12004
See application file for complete search history.

(56) References Cited

U.S. PATENT DOCUMENTS 3,866,607 A     2/1975     Forsythe et al.
4,535,772 A *     8/1985     Sheehan .............. A61B 17/085
                                                                       606/217
(Continued)

FOREIGN PATENT DOCUMENTS

EP     3111855 A1     1/2017
WO     9426173 A2     11/1994
(Continued)

OTHER PUBLICATIONS

International Search Report (PCT/ISA/210) dated Dec. 13, 2018, by the European Patent Office as the International Searching Authority for International Application No. PCT/JP2018/021621.
(Continued)

*Primary Examiner* — Alexander J Orkin
(74) *Attorney, Agent, or Firm* — Buchanan Ingersoll & Rooney PC

(57) ABSTRACT

A medical device and methods for hemostasis in a living body are disclosed. The medical device including a base configured to arranged on an upper surface of the tissue in the living body; a plurality of levers, each of the plurality of levers having a needle arranged on a lower surface thereof and configured to puncture the tissue in the living body, and wherein the plurality of lever are configured to be received with a slot or track of the base; and at least one tie, the at least one tie configured to hold together the plurality levers
(Continued)

and needles upon compressing the tissue in the living body upon moving the plurality of levers inward in the slot or track of the base.

22 Claims, 37 Drawing Sheets

Related U.S. Application Data filed on Jun. 12, 2017, provisional application No. 62/518,225, filed on Jun. 12, 2017.

(51) Int. Cl.
*A61B 17/06* (2006.01)
*A61B 17/12* (2006.01)
*A61B 17/00* (2006.01)
*A61B 17/064* (2006.01)

(52) U.S. Cl.
CPC .... *A61B 17/12* (2013.01); *A61B 2017/00407* (2013.01); *A61B 2017/00668* (2013.01); *A61B 2017/0417* (2013.01); *A61B 2017/0472* (2013.01); *A61B 2017/0641* (2013.01); *A61B 2017/081* (2013.01); *A61B 2017/12004* (2013.01)

(56) References Cited

U.S. PATENT DOCUMENTS

| | | | |
|---|---|---|---|
| 5,234,462 A | 8/1993 | Pavletic | |
| 5,759,193 A | 6/1998 | Burbank et al. | |
| 5,893,879 A * | 4/1999 | Hirshowitz | A61B 17/08 606/218 |
| 7,803,176 B2 * | 9/2010 | Teague | A61B 17/8076 606/300 |
| 8,221,421 B2 * | 7/2012 | Hearn | A61B 17/8076 606/71 |
| 2004/0133218 A1 * | 7/2004 | Charles | A61B 17/083 606/151 |
| 2006/0247681 A1 * | 11/2006 | De Canniere | A61B 17/3478 606/219 |
| 2006/0282104 A1 * | 12/2006 | Williamson | A61B 17/32 606/151 |
| 2009/0118775 A1 | 5/2009 | Burke | |
| 2010/0137817 A1 * | 6/2010 | Hardman | A61M 1/90 604/290 |
| 2013/0138145 A1 | 5/2013 | Von | |
| 2013/0296930 A1 * | 11/2013 | Belson | A61B 17/085 606/216 |
| 2013/0325046 A1 * | 12/2013 | Terwiske | A61B 17/32093 606/167 |
| 2014/0039525 A1 | 2/2014 | Trask | |
| 2014/0039548 A1 * | 2/2014 | Whitman | A61B 17/068 606/215 |
| 2014/0236227 A1 | 8/2014 | Nash et al. | |
| 2015/0164504 A1 | 6/2015 | Atkinson et al. | |
| 2017/0128273 A1 * | 5/2017 | Smith | A61B 17/085 |
| 2017/0240327 A1 * | 8/2017 | Sanders | B65D 63/18 |
| 2018/0193019 A1 * | 7/2018 | Yang | A61B 17/085 |
| 2019/0380704 A1 * | 12/2019 | Fleischmann | A61B 17/08 |

FOREIGN PATENT DOCUMENTS

| | | |
|---|---|---|
| WO | 2011019859 A2 | 2/2011 |
| WO | 2013188884 A1 | 12/2013 |
| WO | 2015191773 A1 | 12/2015 |

OTHER PUBLICATIONS

Written Opinion (PCT/ISA/237) dated Dec. 13, 2018, by the European Patent Office as the International Searching Authority for International Application No. PCT/JP2018/021621.

* cited by examiner

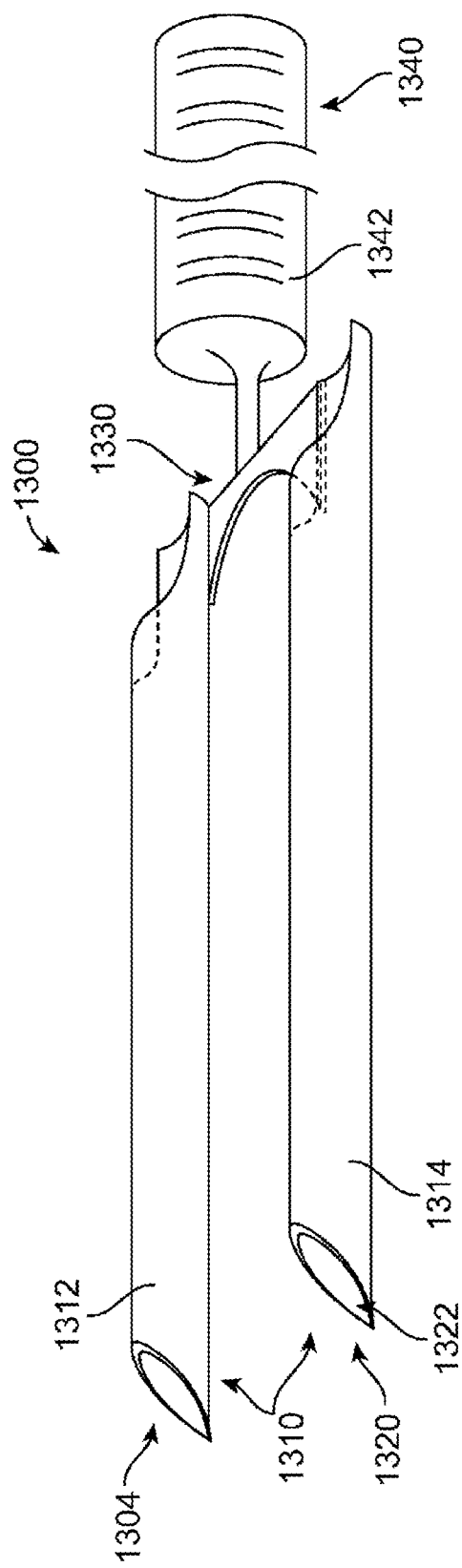

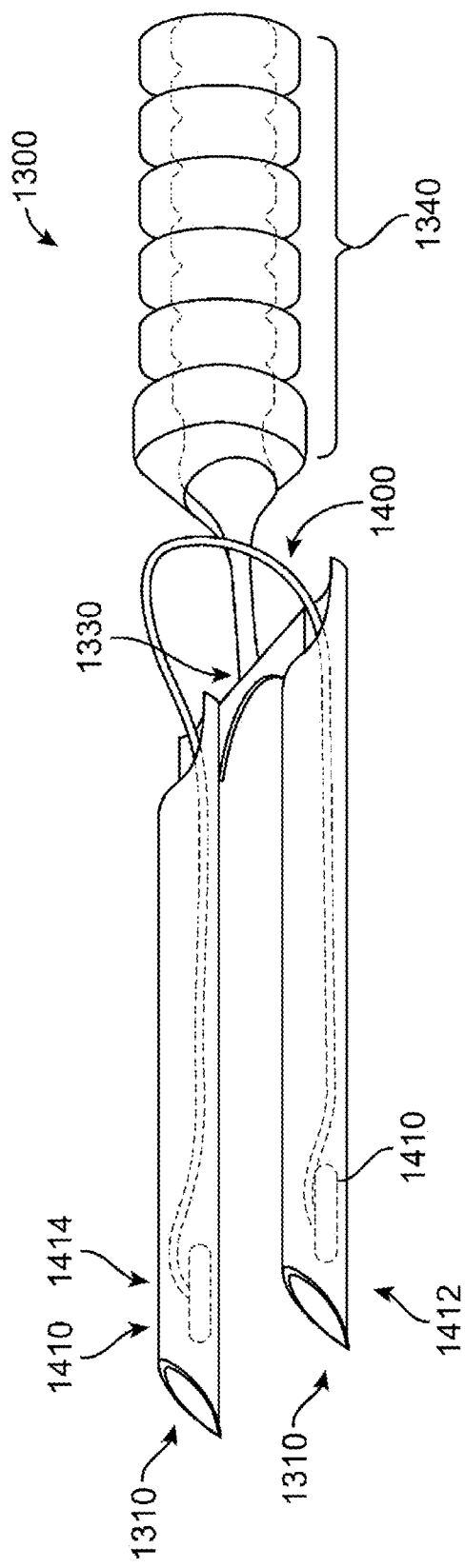

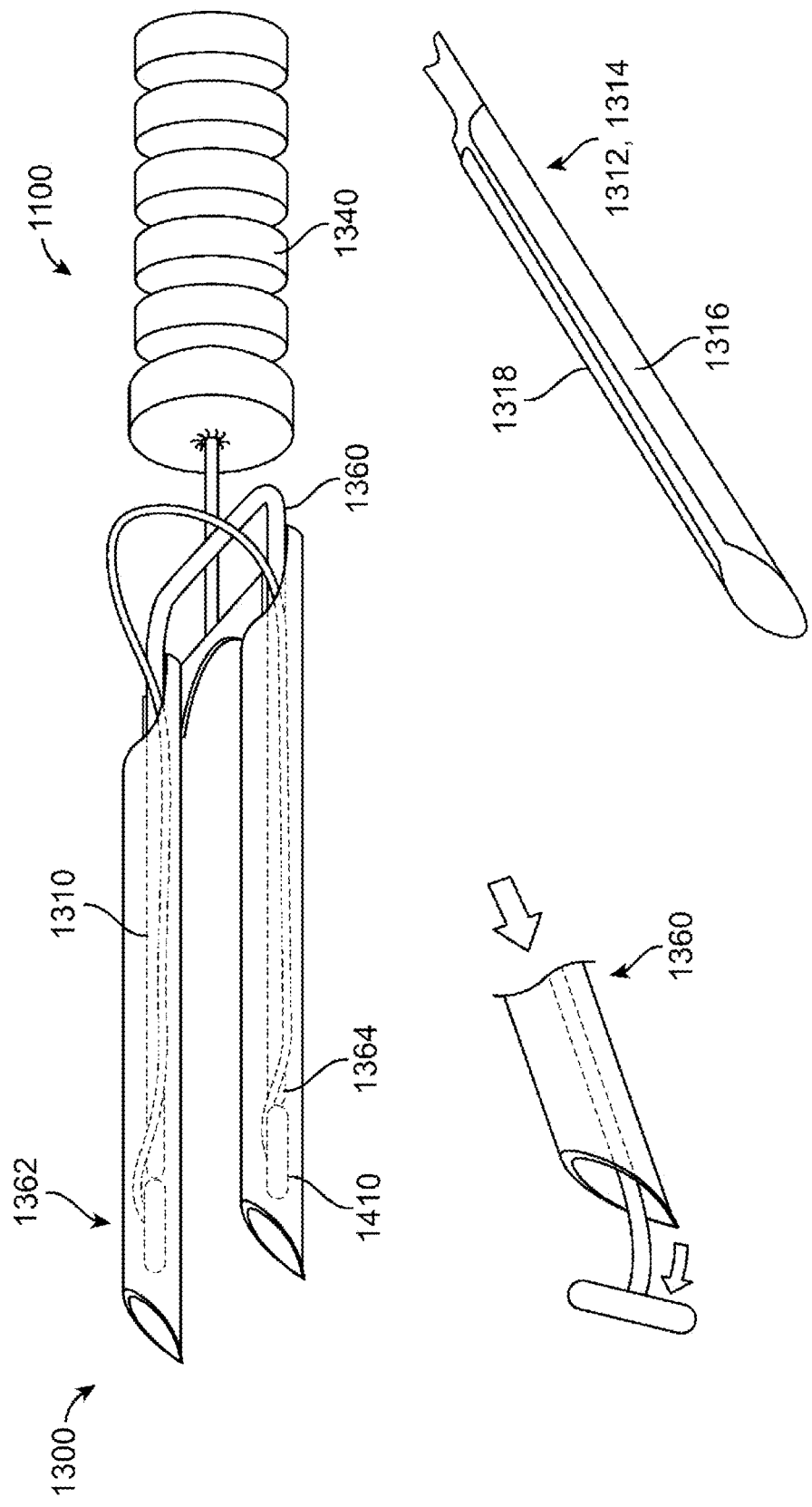

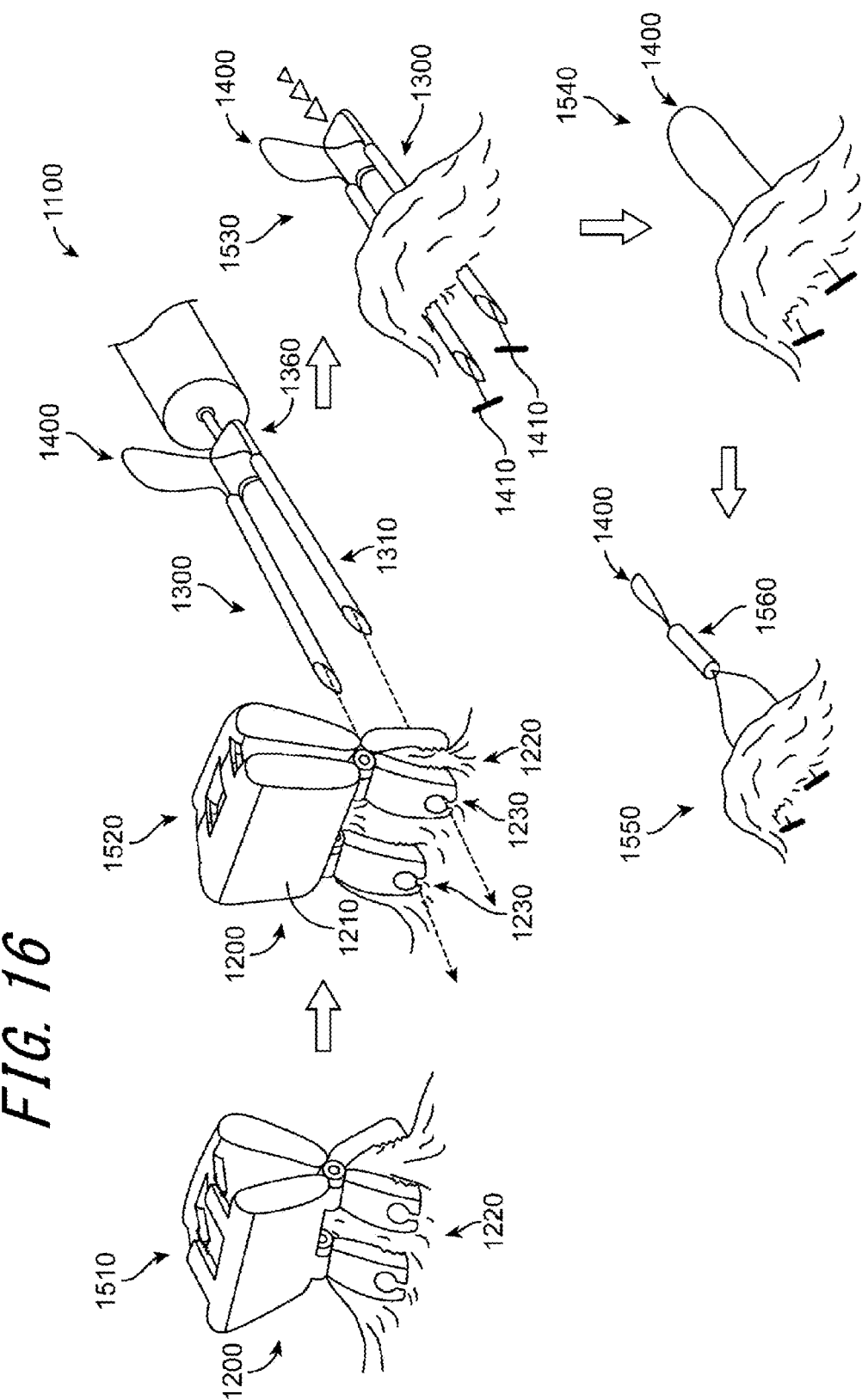

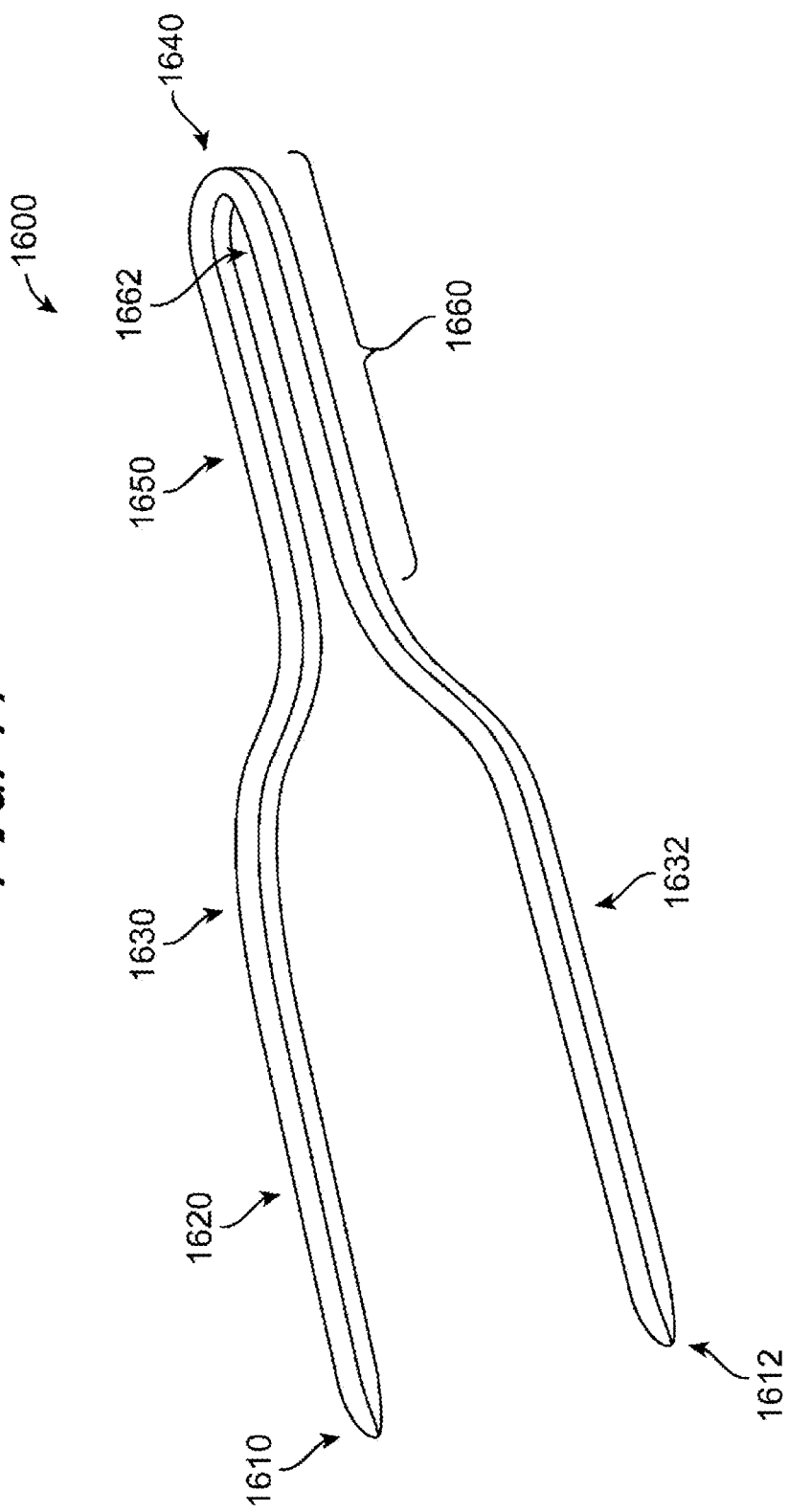

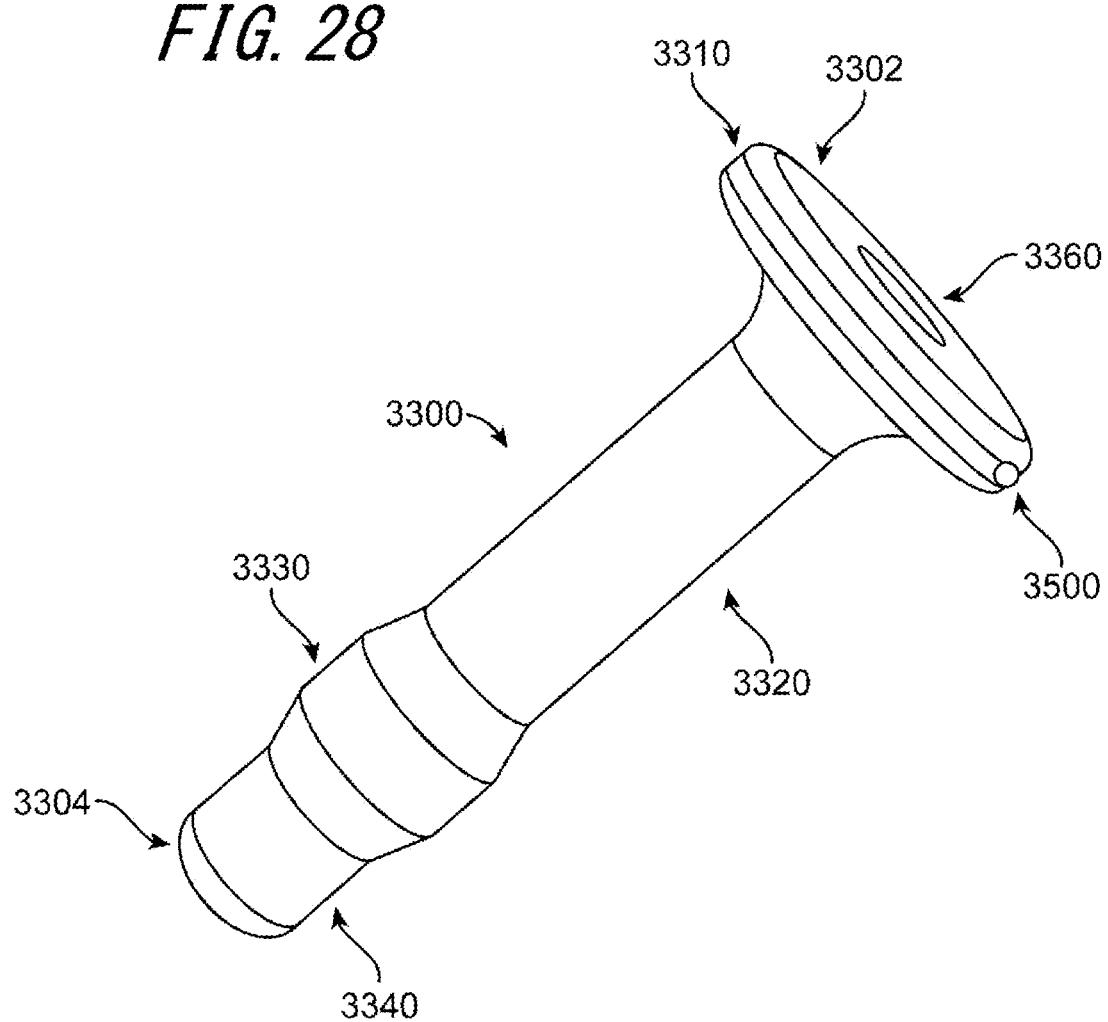

SUBCUTANEOUS TISSUE DEVICE

CROSS-REFERENCES TO RELATED APPLICATIONS

This application claims priority to U.S. Patent Application No. 62/518,225 filed on Jun. 12, 2017, U.S. Patent Application No. 62/518,289 filed on Jun. 12, 2017, and U.S. Patent Application No. 62/518,179 filed on Jun. 12, 2017, the entire content of all three of which is incorporated herein by reference.

TECHNICAL FIELD

The present disclosure generally relates to a medical device, more particularly a subcutaneous tissue devices, subcutaneous plugs, and methods for achieving hemostasis with a compression type subcutaneous tissue device, and more particularly, compression devices, which are configured to compress subcutaneous tissue, for example, to achieve hemostasis at femoral vein access site after cardiac ablation, left atrial appendage closure or mitral valve repair by percutaneous catheter procedure.

BACKGROUND

Known methods of performing hemostasis can include manual compression, figure of eight suturing, and arterial closure device or hemostasis tools. Manual compression is relatively easy; however, one typically must hold compression for 10 to 30 min, back pain due to long bed rest (4 to 6 hours), more likely to bleed again. The figure-of-eight suturing is faster (about 1 min); however, it can require training, potential for perforation (deep puncture), bleeding (shallow suture path), and potential for embolization (too tight). The arterial closure devices have strong hemostatic capability. However, hemostasis tools often have high cost, may require more than one device for a large-bore site, and can potentially injure venous wall, which directly interfaces with the wall.

SUMMARY

It would be desirable to have a subcutaneous tissue device or subcutaneous plug, which can achieve hemostasis in a manner that is more consistent and reliable (thus safer) than the figure-of-eight suturing, can achieve hemostasis that allows the patient to ambulate quickly, can achieve hemostasis on multiple access sites with one device, and can achieve hemostasis on large-diameter access site with one device (current arterial closure devices can require more than one).

(1) A medical device is disclosed for hemostasis in a living body, the medical device comprising: a housing; a central knob; a mechanism housed in the housing, which upon turning the central knob causes a plurality of needles to move towards one another, each of the plurality of needles configured to penetrate a specific depth into the tissue, and compress the tissue to create hemostasis.

(2) In the medical device in (1) described above, the plurality of needles are a pair of an array of needles, which are configured to move towards one another, each of the pair of the array of needles including a plurality of needles (or subdermal components) configured to penetrate the tissue (or skin), and compress the tissue (or skin) to create hemostasis.

(3) In the medical device in (2) described above, a distance between the pair of the array of needles is approximately 20 mm to 40 mm.

(4) In the medical device in (1) described above, further comprising a cutout on the housing configured to receive at least one medical sheath or catheter such that the at least one medical sheath or catheter can pass through the medical device and the medical device can be placed over inserted sheaths, catheters and the like.

(5) In the medical device in (1) described above, the plurality of needles (or subdermal components) are configured to gain traction in the tissue or skin, provide compression, and maintain a relative position until hemostasis is achieved.

(6) In the medical device in (1) described above, the plurality of needles are small gauge needles, which penetrate the skin, and then apply compression to the tissue.

(7) In the medical device in (1) described above, each of the plurality of needles has a length of about 5 mm to 20 mm.

(8) A method is disclosed of achieving hemostasis with the medical device according to the medical device in (1), the method comprising: puncturing the tissue in the living body with the plurality of needles of the medical device; compressing the tissue in the living body by gathering the plurality of needles; and locking the plurality of needles together.

(9) A medical device is disclosed for hemostasis in a living body, the medical device comprising: a base configured to be arranged on an upper surface of the tissue in the living body; a plurality of levers, each of the plurality of levers having a needle arranged on a lower surface thereof and configured to puncture the tissue in the living body, and wherein the plurality of lever are configured to be received with a slot or track of the base; and at least one tie, the at least one tie configured to hold together the plurality levers and needles upon compressing the tissue in the living body upon moving the plurality of levers inward in the slot or track of the base.

(10) In the medical device in (9) described above, the plurality of levers are four, and the at least one tie is a pair of ties.

(11) In the medical device in (9) described above, further comprising a locking member, the locking member configured to secure the at least one tie.

(12) In the medical device in (9) described above, each of the needles has a length of about 5 mm to 20 mm from the lower surface of the lever.

(13) In the medical device in (9) described above, each of the plurality of needles has an angled tip, and wherein the angled tip points inward towards a center of the medical device.

(14) In the medical device in (9) described above, the base is a rectangular plate having one or more openings or wedges in the rectangular plate, the one or more openings or wedges configured to receive at least one medical sheath or catheter such that the at least one medical sheath or catheter can pass through the medical device and the medical device can be placed over inserted sheaths, catheters and the like.

(15) In the medical device in (9) described above, the at least one tie is a single loop tie.

(16) In the medical device in (9) described above, the slot or track of the base is arranged on a lower surface of the base and the plurality of levers disengage from the base upon reaching a center of the base.

(17) In the medical device in (16) described above, at least a portion of the base disengages with the plurality of levers upon reaching the center of the base.

(18) A method is disclosed of achieving hemostasis with the medical device according to claim 9, the method comprising: puncturing the tissue in the living body with the plurality of needles of the medical device; compressing the tissue in the living body by gathering the plurality of needles; and locking the plurality of needles together.

(19) In the method in (18) described above, each of the plurality of needles are L-shaped needles.

(20) In the method in (18) described above, removing the base after compressing the tissue in the living body by gathering the plurality of needles and/or locking the plurality of needles together.

(21) A method is disclosed of achieving hemostasis with a medical device, the method comprising: placing the medical device on tissue in a living body; puncturing the tissue with C-shaped needles of the medical device with sutures; removing the base and the C-shaped needles from the tissue; and compressing and holding the tissue together with the sutures.

(22) In the method in (21) described above, the sutures form a figure-of-8 closure method.

(23) A subcutaneous tissue device configured to achieve hemostasis is disclosed, the device comprising: a pinching device configured to pinch tissue of a living body, the pinching device having a pair of actuating grips, a pair of pinching jaws, a pinching jaw hole in each of the pair of pinching jaws, and a pinching jaw slot in each of the pair of pinching jaws; and a needle configured to be received within the pinching jaw hole in each of the pair of pinching jaw and pierce the tissue of the living body, the needle comprising a pair of spaced apart hollow needles, which are connected at a proximal end and configured to receive a suture, which is configured to cinch the tissue together.

(24) In the subcutaneous tissue device in (23) described above, a distance between the pinching jaw holes is approximately 20 mm to 40 mm.

(25) In the subcutaneous tissue device in (23) described above, further comprising: a gap between a lower edge of the pair of actuating grips and an upper edge of the pair of pinching jaws such that at least one medical sheath or catheters can pass through the subcutaneous tissue device and the subcutaneous tissue device can be placed over inserted sheaths, catheters and the like.

(26) In the subcutaneous tissue device in (23) described above, the pair of actuating grips each have a locking ratchet, which locks the pair of actuating grips to one another.

(27) In the subcutaneous tissue device in (23) described above, a proximal end and a distal end of the needle are open to receive the suture.

(28) In the subcutaneous tissue device in (23) described above, each of the pair of spaced apart needles on a distal end has an angled tip.

(29) In the subcutaneous tissue device in (23) described above, further comprising: a suture configured to be received in the hollow portion of the pair of spaced apart hollow needles, the suture having a pair of anchors on each end of the suture.

(30) In the subcutaneous tissue device in (23) described above, further comprising: a grip on a proximal end of the needle.

(31) In the subcutaneous tissue device in (23) described above, a slot on a spine of each of the pair of spaced apart hollow needles, the slot configured to allow the suture to be removed from the spaced apart hollow needles.

(32) A method is disclosed of achieving hemostasis, the method comprising: pinching tissue of a living body with a pinching device having a needle guide; puncturing the tissue of the living body with a needle having a suture through the needle guide on the pinching device; removing the pinching device and the needle; and holding the tissue together with the suture.

(33) In the method in (32) described above, the pinching device comprises: a pair of actuating grips, a pair of pinching jaws, a pinching jaw hole in each of the pair of pinching jaws, and a pinching jaw slot in each of the pair of pinching jaws.

(34) In the method in (32) described above the needle comprises: a pair of spaced apart hollow needles, which are connected at a proximal end and configured to receive the suture.

(35) A subcutaneous tissue device configured to achieve hemostasis is disclosed, the device comprising: a pinching device configured to pinch tissue of a living body, the pinching device having a pair of actuating grips, a pair of pinching jaws, a pinching jaw hole in each of the pair of pinching jaws, and a pinching jaw slot in each of the pair of pinching jaws; and a hemostatic pin, the hemostatic pin comprising a pair of distal tips, a main body having a pair of spaced apart member, which converge on a proximal end.

(36) In the subcutaneous tissue device in (35) described above, the proximal end of the hemostatic pin has a grip portion.

(37) A method is disclosed of achieving hemostasis with the pinching device and the hemostatic pin in (35) described above, the method comprising: pinching tissue of a living body with the pinching device; puncturing the tissue of the living body with the hemostatic pin; removing the pinching device; and holding the tissue together with the hemostatic pin.

(38) In the method in (37) described above, further comprising: placing a safety cap on the pair of distal tips of the hemostatic pin.

(39) A pinching device is disclosed for hemostasis by pinching tissue of a living body, the pinching device comprising: a base member; a pair of a passive spring members, each of the passive spring members including a handle, a hinged spring member, and a wire arm; and wherein the wire arms are configured to be spring loaded inward and upon pressing on the handles, the wire arms open such that the pinching device can be placed flat onto the tissue, and upon releasing the handles, the wire arms provide compression to the tissue to achieve hemostasis.

(40) In the pinching device in (39) described above, a distance between the wire arms is approximately 20 mm to 40 mm.

(41) In the pinching device in (39) described above, further comprising: a front cutout section on the base member configured to allow at least one medical sheath to pass through the front cutout section.

(42) In the pinching device in (39) described above, the base member includes two side cutout sections, the two side cutout sections are configured to receive the passive spring members.

(43) A method is disclosed of achieving hemostasis with the pinching device in (39) described above, the method comprising: pinching the tissue with the pinching device; and holding the tissue with pinching device.

(44) A subcutaneous plug configured to achieve hemostasis in a living body is disclosed, the subcutaneous plug comprising: a proximal portion on a proximal end; a middle portion extending between the proximal portion to an expanded portion; and a distal portion extending from the expanded portion to a distal end, the distal portion having an inner surface configured to be pushed by a pusher, and wherein an outer diameter of the expanded portion is greater than an outer diameter of the proximal and the middle portions, and the expanded portion is configured to seal off the bleeding in a wound channel.

(45) In the subcutaneous plug in (44) described above, the expanded portion is constructed from a series of cylindrical members, which includes a pair of angled side sections, and a center section have a greater diameter than a diameter of the middle portion and the distal portion.

(46) In the subcutaneous plug in (44) described above, a guidewire lumen extending from the proximal end to the distal end.

(47) In the subcutaneous plug in (46) described above, a self-closing hole on the distal end.

(48) In the subcutaneous plug in (47) described above, the self-closing hole is a small hole in a membrane at the distal end or a small axial hole in the center of a cylinder at the distal portion, and wherein the self-closing hole is configured to close at its passive state by the elasticity of a material of the subcutaneous plug.

(49) In the subcutaneous plug in (44) described above, the proximal portion is in a shape of a cylindrical plate.

(50) In the subcutaneous plug in (44) described above, further comprising: an inflate port arranged on the proximal portion of the subcutaneous plug configured to provide a fluid to inflate the expanded portion of the subcutaneous plug.

(51) In the subcutaneous plug in (44) described above, the subcutaneous plug is a cylindrical silicone plug.

(52) In the subcutaneous plug in (44) described above, the subcutaneous plug has a length of about 5 mm to 20 mm, and a diameter of between 2 mm to 7 mm.

(53) In the subcutaneous plug in (52) described above, the length of the subcutaneous plug is 10 mm.

(54) A subcutaneous plug assembly is disclosed, the assembly comprising: a subcutaneous plug configured to achieve hemostasis in a living body, the subcutaneous plug including a proximal portion on a proximal end; a middle portion extending between the proximal portion to an expanded portion; and a distal portion extending from the expanded portion to a distal end, the distal portion having an inner surface configured to be pushed by a pusher, and wherein an outer diameter of the expanded portion is greater than an outer diameter of the proximal and the middle portions, and the expanded portion is configured to seal off the bleeding in a wound channel; and a pusher for engaging and pushing the distal portion of the subcutaneous plug.

(55) In the subcutaneous plug in (54) described above, the pusher comprises: a first cylindrical member on a proximal portion and a second cylindrical member on a distal portion, and wherein an outer diameter of the distal portion is smaller than an outer diameter of the proximal portion.

(56) In the subcutaneous plug in (55) described above, the second cylindrical member is configured to fit within a lumen of the subcutaneous plug.

(57) In the subcutaneous plug in (55) described above, the pusher includes a guidewire lumen configured to receive a guidewire, which extends from a proximal end to a distal end of the pusher.

(58) A method is disclosed of achieving hemostasis in a living body, the method comprising: advancing a subcutaneous plug over a guidewire into a wound channel of the living body with a pusher; removing the guidewire and the pusher; and achieving hemostasis with the subcutaneous plug.

(59) In the method in (58) described above, further comprising: placing the subcutaneous plug in the wound channel by pushing an inner surface of a distal portion of the subcutaneous plug with the pusher.

(60) In the method in (58) described above, further comprising: inflating an expanded portion of the subcutaneous plug within the wound channel.

(61) In the method in (58) described above, further comprising: removing the subcutaneous plug from the wound channel after achieving hemostasis.

(62) In the method in (58) described above, the wound channel is at a femoral vein access site after cardiac ablation, a left atrial appendage closure, or a mitral valve repair by percutaneous catheter procedure.

(63) In the method in (58) described above, wherein the subcutaneous plug comprises: a proximal portion on a proximal end; a middle portion extending between the proximal portion to an expanded portion; and a distal portion extending from the expanded portion to a distal end, the distal portion having an inner surface configured to be pushed by the pusher, and wherein an outer diameter of the expanded portion is greater than an outer diameter of the proximal and the middle portions, and the expanded portion is configured to seal off the bleeding in a wound channel.

BRIEF DESCRIPTION OF DRAWINGS

FIG. 14A is a perspective view of a needle of the medical device as shown in FIG. 12 in accordance with an exemplary embodiment.

FIG. 14B is another perspective view of a needle with a suture for use with the medical device as shown in FIG. 12 in accordance with an exemplary embodiment.

FIG. 15 is a perspective view of a needle for use with the medical device as shown in FIG. 12 in accordance with an exemplary embodiment.

FIG. 16 is an illustration of a use of the medical device for hemostasis in accordance with an exemplary embodiment.

FIG. 17 is a perspective view of a hemostatic pin in accordance with an exemplary embodiment.

FIG. 28 is a perspective view of a subcutaneous plug assembly in accordance with another exemplary embodiment.

DETAILED DESCRIPTION

Figure 1:
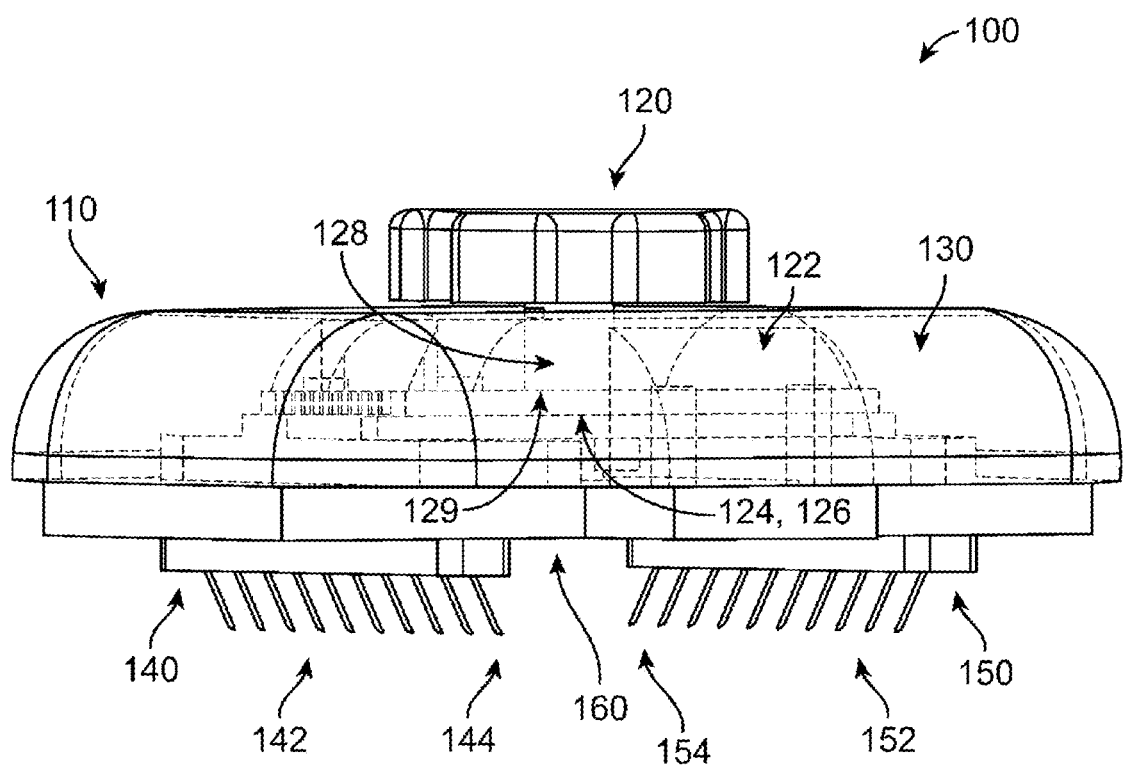
FIG. 1 is a schematic view of a medical device for hemostasis in accordance with an exemplary embodiment.

Hereinafter, embodiments of the present disclosure will be described with reference to the drawings. In order to facilitate description, dimensional ratios in the drawings are exaggerated, and thus are different from actual ratios in some cases.

FIG. 1 is a schematic view of a medical device 100 for hemostasis in accordance with an exemplary embodiment. As shown in FIG. 1, the medical device 100 includes a housing 110, a central knob 120, a mechanism 130 housed in the housing 110, which upon turning the central knob 120 causes a pair of an array of needles 140, 150 to move towards one another. In accordance with an exemplary embodiment, when the central knob 120 is turned, a rack-and-pinion system 122 moves each rack 124, 126 in the opposite directions. The central knob 120 is on a shaft 128 that is connected to a pinion gear 129 whose center is coaxial to the shaft 128. Two racks 124, 126 are placed on opposite sides of the pinion gear such that when the knob 120 is turned each rack 124, 126 moves in the opposite direction. In accordance with an exemplary embodiment, the end of each rack 124, 126 is connected to one of the respective array of needles 140, 150. To keep the array of needles 140, 150 from tilting, each rack 124, 126 may be supported by a parallel guide shaft placed on the opposite side of the pinion gear 129 that would slide with the rack 124, 126 when it is driven by the pinion gear 129. In accordance with an alternative embodiment, (to the sliding support guide shafts), there may be another pinion gear stacked above or below the primary pinion gear described above. Two same-size pinion gears may be on each side of this secondary pinion gear and have a corresponding rack on each side of them. The ends of these racks (not shown) can also be connected to the array of needles 140, 150, and can be configured to match the movement of the two primary racks described above to provide more drive force and stability to the array of needles 140, 150.

In accordance with an exemplary embodiment, each of the pair of array of needles 140, 150 includes a plurality of needles (or subdermal components) 142, 152 configured to penetrate a specific depth into the tissue (or skin), and compress the tissue (or skin) to create hemostasis. In accordance with an exemplary embodiment, each of the medical devices 100, 200, 300, 400, 500, 600, 700 as disclosed herein are configured to pinch or compress the tissue of living body above the blood vessel.

In accordance with an exemplary, the plurality of needles (or subdermal components) 142, 152 are configured to gain traction in the tissue or skin, provide compression, and maintain a relative position until hemostasis is achieved. For example, in accordance with an exemplary embodiment, the needles 142, 152 can be small gauge needles, which penetrate the skin, and then apply compression to the wound change. The plurality of needles 142, 152 can be removed after hemostasis is achieved and the wound no longer will bleed. In accordance with an exemplary embodiment, the needles 142, 152 can be removed with little or no residual bleeding from the needle punctures.

In accordance with an exemplary embodiment, the needles 142, 152, should be a gauge, which is small enough that they can be removed without causing significant bleeding, the number, size, length, and geometric arrangement of the needles can be optimized to provide compression to close the wound left by an access sheath. In accordance with an exemplary embodiment, a diameter of each of the needles should be approximately 0.5 mm to 1.5 mm, and the array of needles 140, 150 can have an overall width of approximately 20 mm to 40 mm. In accordance with an exemplary embodiment, when the array of needles 140, 150 are in an open position or configuration (i.e., have not started to move inward), a distance between an inner edge 144, 154 of each of the array of needles 140, 150 should be approximately 20 mm to 40 mm. When the array of needles are fully closed, (i.e., the array of needles 140, 150 have moved inward), the distance between the inner edge 144, 154 of each of the array of needles 140, 150 should be approximately 1 mm to 10 mm. In addition, the angle and contour of the needles 142, 152 can be configured to be held in place while compression is being applied. In accordance with an exemplary embodiment, the needles 142, 152 can have length of about 5 mm to 20 mm.

Figure 2A:
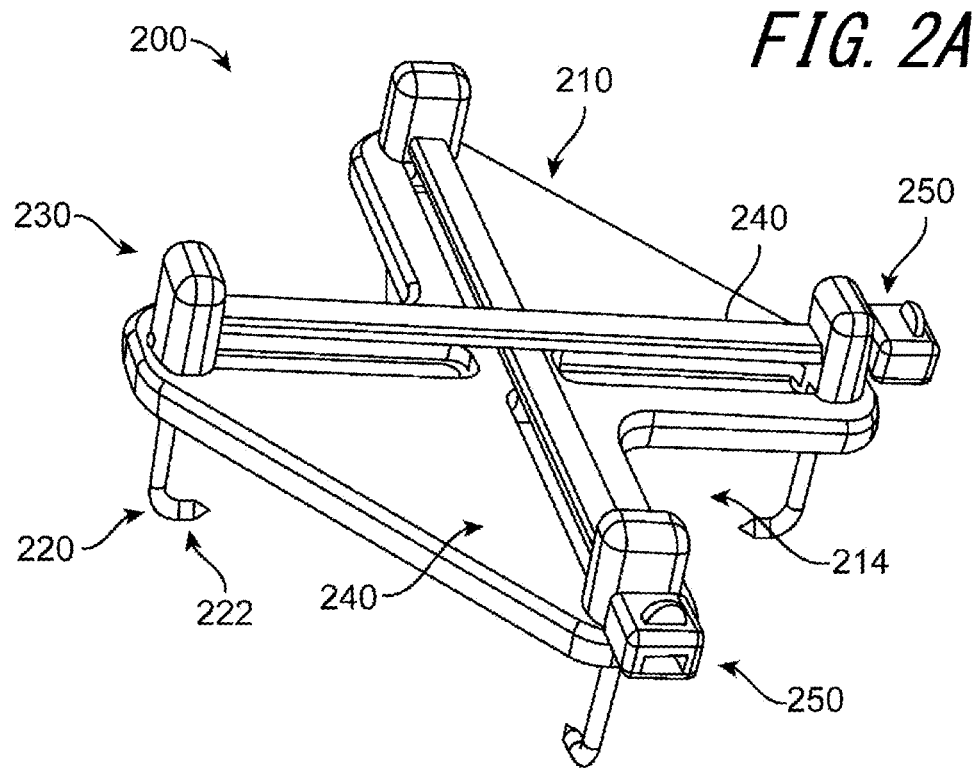
FIG. 2A is a perspective view of a medical device having a straight tie in accordance with another exemplary embodiment.
Figure 2B:
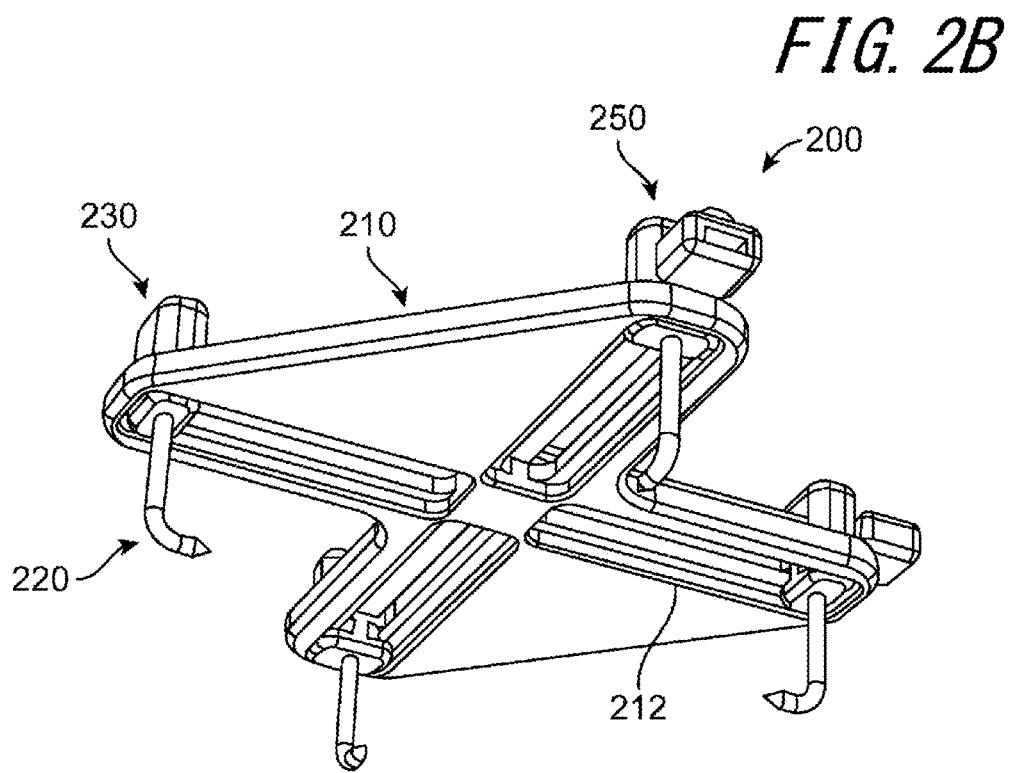
FIG. 2B is a perspective view of the medical device of FIG. 2A viewed from the underside in accordance with an exemplary embodiment.

FIGS. 2A and 2B are perspective views of a medical device 200 having a straight tie in accordance with another exemplary embodiment. As shown in FIGS. 2A and 2B, the medical device 200 can include a base 210, a plurality of needles 220, a plurality of levers 230, preferably four (4) levers 230, a pair of ties 240, and a locking feature or locking element 250. Each of the plurality of needles 220, which preferably have a length of about 5 mm to 20 mm. In accordance with an exemplary embodiment, each of the plurality of needles 220 has a tip 222, which can be an angled tip (or L-shaped), which, for example, points inward towards a center of the medical device 200.

As shown in FIGS. 2A and 2B, the base 210 can be rectangular plate having one or more openings or wedges 214 therein to allow sheaths, catheters and the like to pass to be passed through the medical device 200. In accordance with an exemplary embodiment, when the needles 220 are in their fully opened configuration, the distance between the tips 222 should be 20 mm to 40 mm. When the needles 220 are in a fully closed position, the distance between the tips 222 should be 1 mm to 10 mm. The base 210 includes a plurality of slots or tracks 212. Each of the plurality of slots or tracks 212, which preferably are four, is configured to receive a single lever 230 and a needle extending downward from the lever 230. A lower edge or portion of the lever 230 is configured to fit or rest within the slot or track 212 without falling through the slot or track 212. The slots 212 extend from each corner of the base 210 inward at right angles to one another or in the shape of an "X".

In addition, the pair of ties 240 extend from opposite corners and cross in the middle of the base 210. Each of the ties 240 are fixed to one of the two levers 230 and the other lever 230 includes an opening configured to receive the tie 240. In accordance with an exemplary embodiment, a locking feature or locking element 250 is arranged adjacent to the lever 230 in which the tie 240 extends. The locking feature or locking element 250 preferably includes an opening or small open case (not shown), which includes a ratchet configured to engage an integrated gear rack on the tie 240. In accordance with an exemplary embodiment, the pair of ties 240 are preferably nylon, for example, a flexible nylon tape. In accordance with an alternative embodiment, rather than a locking member, the levers 230 can include the small open case and ratchet configured to engage the integrated gear rack on the tie 240.

Figure 2C:
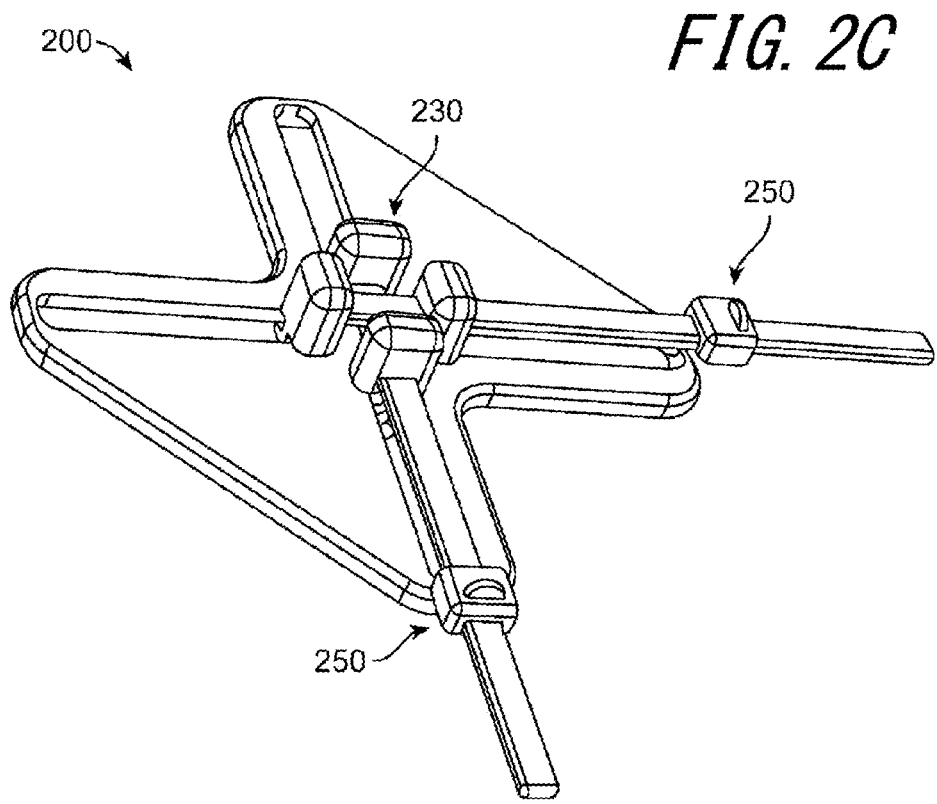
FIG. 2C is a perspective view of the medical device of FIGS. 2A and 2B in use in accordance with an exemplary embodiment.
Figure 2D:
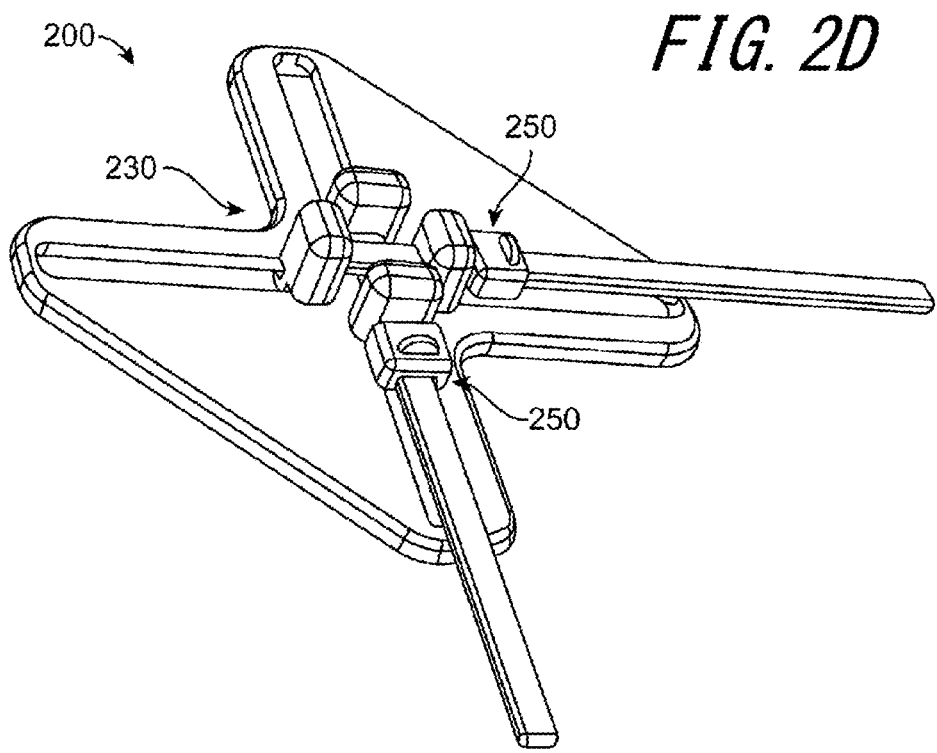
FIG. 2D is a perspective view of the medical device of FIGS. 2A and 2B in use in accordance with an exemplary embodiment.

FIGS. 2C and 2D are perspective views of the medical device of FIGS. 2A and 2B in use in accordance with an exemplary embodiment. As shown in FIG. 2C in use, the medical device 200 is placed on the tissue (or skin) of the patient. The four needles compress the tissue, for example, at a depth of 5 mm to 20 mm. The operator moves the four levers 230 from each of the corners inward by penetrating the tissue or skin with the tips 222 of the needles 220 meeting at the center of the base 210. In accordance with an exemplary embodiment, the two locking feature or locking element 250 can be moved inward as shown in FIG. 2D to lock the needles 220 in place.

Figure 3A:
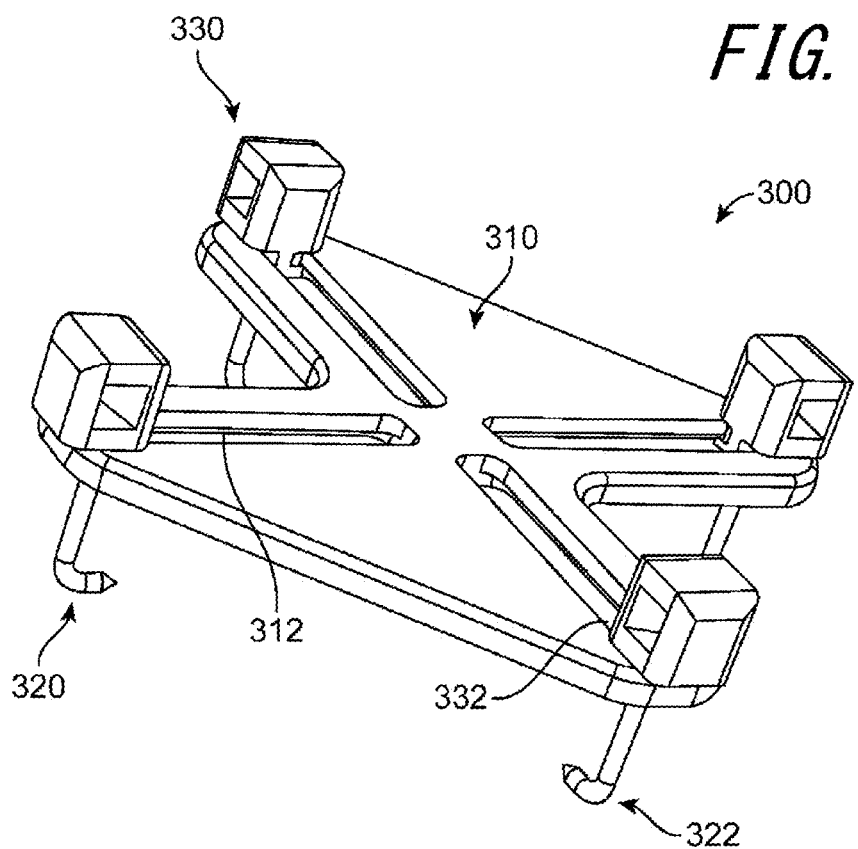
FIG. 3A is a perspective view of a medical device in accordance with an exemplary embodiment.
Figure 3B:
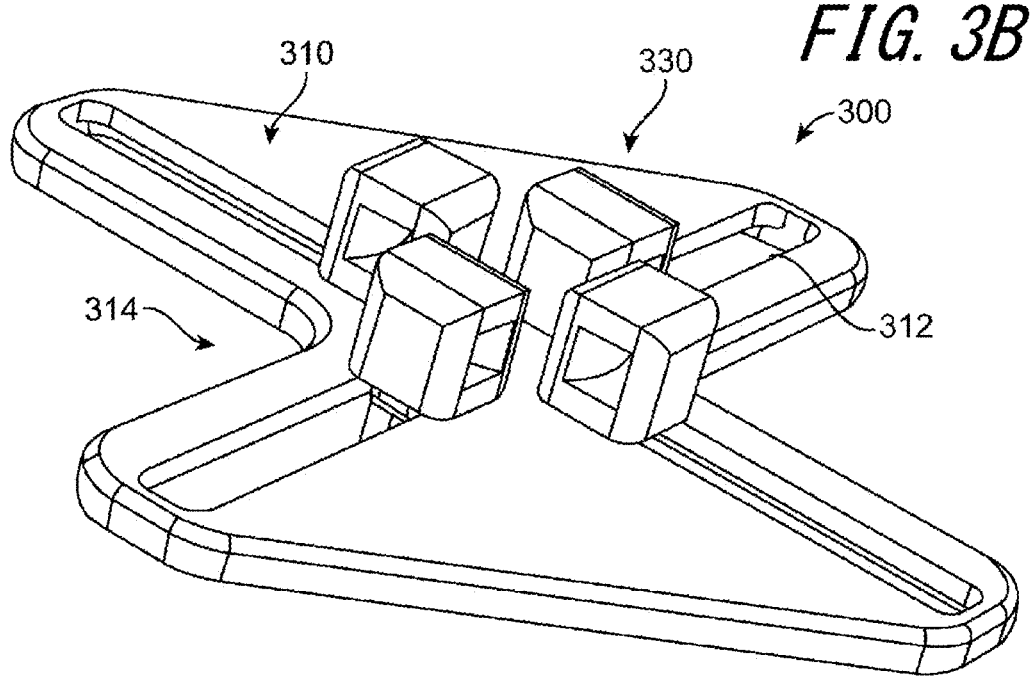
FIG. 3B is a perspective view of the medical device as shown in FIG. 3A in accordance with an exemplary embodiment.
Figure 4:
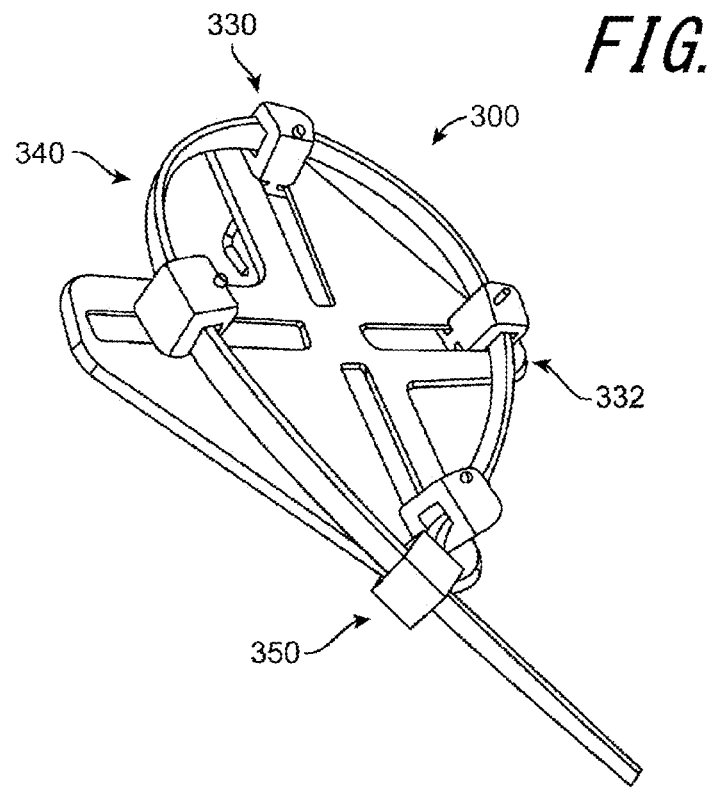
FIG. 4 is perspective view of the medical device having a loop tie as shown in FIGS. 3A and 3B view from above in accordance with an exemplary embodiment.

FIGS. 3A and 3B are perspective views of a medical device 300 in accordance with an exemplary embodiment. As shown in FIG. 3A, the medical device 300, which can be used with a loop tie 340 as shown in FIG. 4, can include a base 310, a plurality of needles 320, and a plurality of levers 330, preferably four (4) levers. Each of the plurality of needles 320 preferably have a length of about 5 mm to 20 mm. In accordance with an exemplary embodiment, each of the plurality of needles 320 can have a tip 322, which can be an angled tip, which, for example, points inward towards a center of the medical device 300.

As shown in FIGS. 3A and 3B, the base 310 can be rectangular plate having one or more openings or wedges 314 therein to allow sheaths, catheters and the like to pass to be passed through the medical device 300. In accordance with an exemplary embodiment, when the needles 320 are in their fully opened configuration, the distance between the tips 322 should be 20 mm to 40 mm. When the needles 320 are in a fully closed position, the distance between the tips 322 should be 1 mm to 10 mm. The base 310 includes a plurality of slots or tracks 312. Each of the plurality of slots or tracks 312, which preferably are four, is configured to receive a single lever 330 and a needle 320 extending downward from the lever 330. A lower edge or portion of the lever 330 is configured to fit or rest within the slot or track 312 without falling through the slot or track 312. The slots 312 extend from each corner of the base 310 inward at right angles to one another or in the shape of an "X".

Figure 5:
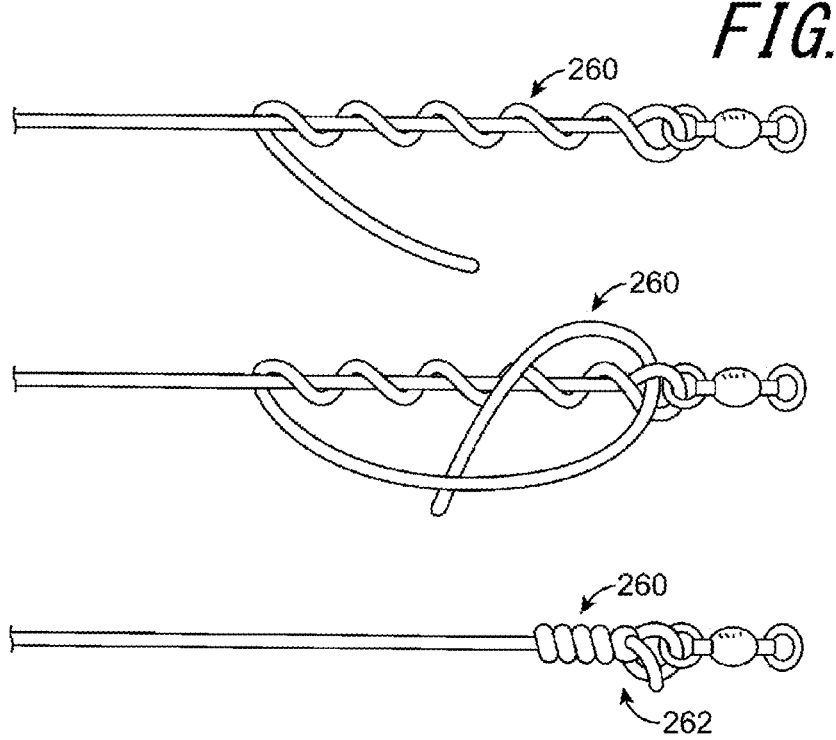
FIG. 5 is an illustration of how a clinch knot is tied in accordance with an exemplary embodiment.
Figure 6A:
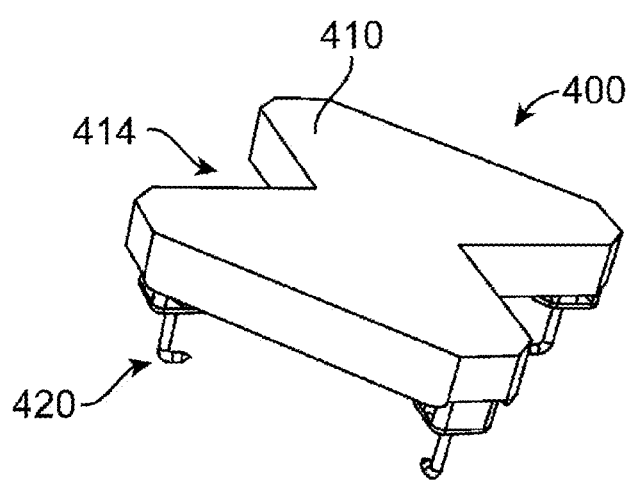
FIG. 6A is a perspective view of a medical device having a loop tie and suture structure in accordance with an exemplary embodiment.
Figure 6B:
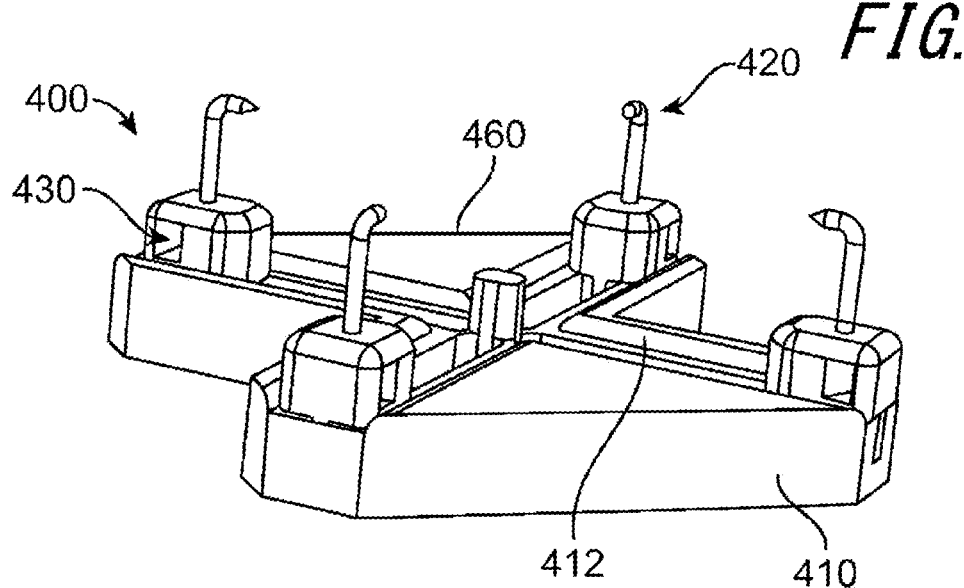
FIG. 6B is a perspective view of a medical device having a loop tie and suture structure in accordance with an exemplary embodiment.
Figure 6C:
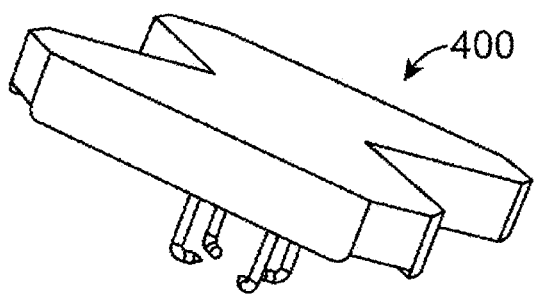
FIG. 6C is a perspective view of a medical device having a loop tie and suture structure in accordance with an exemplary embodiment.
Figure 6D:
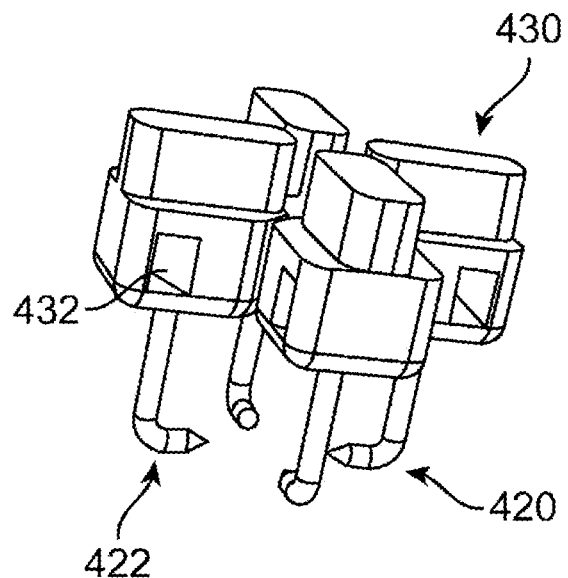
FIG. 6D is a perspective view of a medical device having a loop tie and suture structure in accordance with an exemplary embodiment.
Figure 6E:
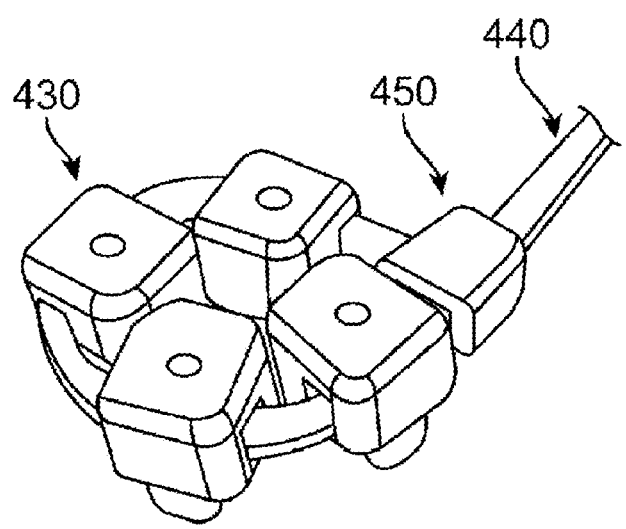
FIG. 6E is a perspective view of a medical device having a loop tie and suture structure in accordance with an exemplary embodiment.

FIG. 4 is perspective view of the medical device having a loop tie as shown in FIGS. 3A and 3B view from above in accordance with an exemplary embodiment. As shown in FIG. 4, a single loop tie 340 with a locking member 350 can be used to fix the needles 320 and levers 330 upon moving them towards the center of the device 300. Each of the levers 330 includes an opening 332 in which the tie 340 can freely move within. In accordance with an exemplary embodiment, the locking member 350 preferably includes an opening or small open case (not shown), which includes a ratchet configured to engage an integrated gear rack on the tie 340. In accordance with an exemplary embodiment, the tie 340 is preferably nylon, for example, a flexible nylon tape. Alternatively, rather than a tie 240, 340 in the form of a nylon tape, a suture 260 tied in a clinch knot 262 as shown in FIG. 5 can be used.

FIGS. 6A-6E are perspective views of a medical device 400 having a loop tie and suture structure in accordance with an exemplary embodiment. As shown in FIGS. 6A-6E, the medical device can include a base 410, a plurality of needles 420, and a plurality of levers 430, preferably four (4) levers. Each of the plurality of needles 420, which preferably have a length of about 5 mm to 20 mm. In accordance with an exemplary embodiment, each of the plurality of needles 420 can have an angled tip 422, which, for example, points inward towards a center of the medical device 400.

As shown in FIGS. 6A-6E, the base 410 can be rectangular plate having one or more openings or wedges 414 therein to allow sheaths, catheters and the like to be passed through the medical device 400. In accordance with an exemplary embodiment, when the needles 420 are in their fully opened configuration, the distance between the tips 422 should be 20 mm to 40 mm. When the needles 420 are in a fully closed position, the distance between the tips 422 should be 1 mm to 10 mm. The base 410 includes a plurality of slots or tracks 412. Each of the plurality of slots or tracks 412, which preferably are four, is configured to receive a single lever 430 and a needle 420 extending downward from the lever 430. In accordance with an exemplary embodiment, an upper portion (not shown) of the lever 430 is configured to fit or rest within the slot or track 412. The slots 412 extend from each corner of the base 410 inward at right angles to one another or in the shape of an "X". In accordance with an exemplary embodiment, the slots or tracks 412 can be configured that upon reaching the center of the base 410, the levers 430 and needles 420 can be separated or disengaged from the base 410.

In accordance with an exemplary embodiment, a single loop tie 440 with a locking member 450 can be used to fix the needles 420 and levers 430 upon moving them towards the center of the device 400. Each of the levers 430 includes an opening 432 in which the tie 440 can freely move within. In accordance with an exemplary embodiment, the locking member 450 preferably includes an opening or small open case (not shown), which includes a ratchet configured to engage an integrated gear rack on the tie 440. In accordance with an exemplary embodiment, the tie 440 is preferably nylon, for example, a flexible nylon tape. Alternatively, rather than a tie 440 in the form of a nylon tape, a suture tied in a clinch knot as shown in FIG. 5 can be used.

Figure 7A:
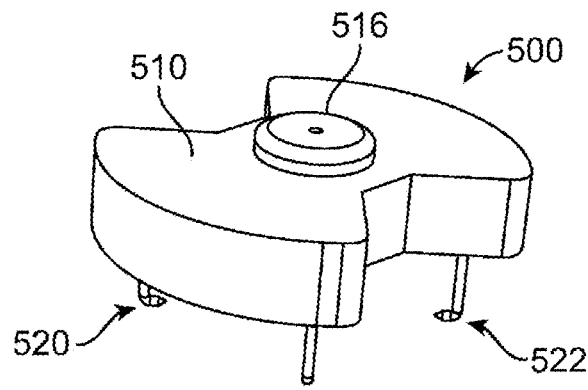
FIG. 7A is a perspective view of a medical device having a loop tie and suture structure in accordance with another exemplary embodiment.
Figure 7B:
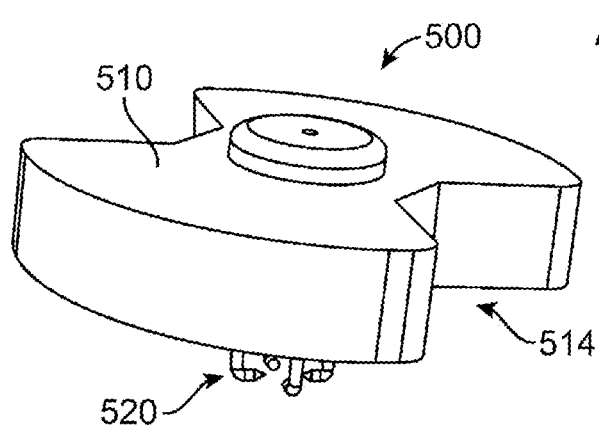
FIG. 7B is a perspective view of a medical device having a loop tie and suture structure in accordance with another exemplary embodiment.
Figure 7C:
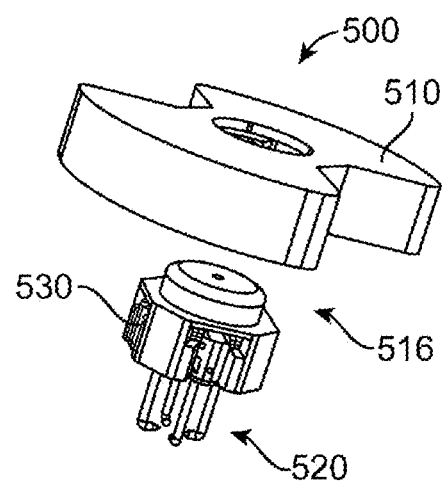
FIG. 7C is a perspective view of a medical device having a loop tie and suture structure in accordance with another exemplary embodiment.

FIGS. 7A-7C are perspective views of a medical device 500 having a loop tie and suture structure in accordance with another exemplary embodiment. As shown in FIGS. 7A-7C, the medical device can include a base 510, a plurality of needles 520, and a plurality of levers 530, preferably four (4) levers. Each of the plurality of needles 520, which preferably have a length of about 5 mm to 20 mm. In accordance with an exemplary embodiment, each of the plurality of needles 520 can have an angled tip 522, which, for example, points inward towards a center of the medical device 500.

As shown in FIGS. 7A-7C, the base 510 can be rectangular plate having one or more openings or wedges 514 and/or rounded edges therein to allow sheaths, catheters and the like to pass to be passed through the medical device 500. In accordance with an exemplary embodiment, when the needles 520 are in their fully opened configuration, the distance between the tips 522 should be 20 mm to 40 mm. When the needles 520 are in a fully closed position, the distance between the tips 522 should be 1 mm to 10 mm. The base 510 includes a plurality of slots or tracks 512. Each of the plurality of slots or tracks 512, which preferably are four, is configured to receive a single lever 530 and a needle 520 extending downward from the lever 530. In accordance with an exemplary embodiment, an upper portion (not shown) of the lever 530 is configured to fit or rest within the slot or track 512. The slots 512 extend from each corner of the base 510 inward at right angles to one another or in the shape of an "X". In accordance with an exemplary embodiment, the slots or tracks 512 can be configured that upon reaching the center of the base 510, the levers 530 and needles 520 can be separated or disengaged from the base 510 with a center portion 516 of the base 510.

Figure 8A:
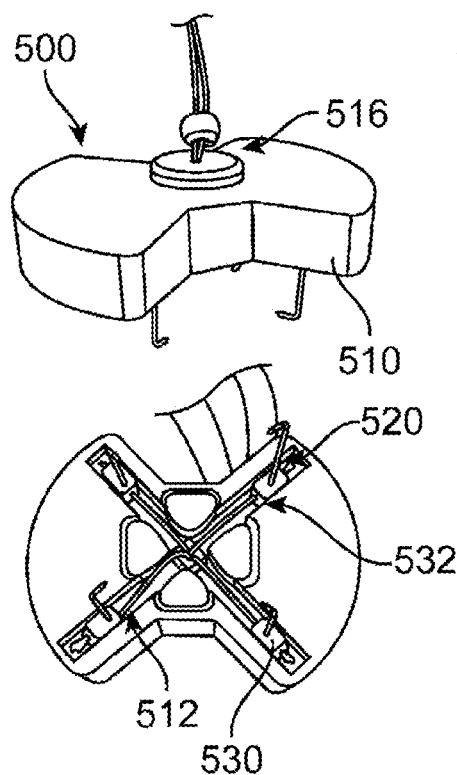
FIG. 8A is a perspective view of the medical device as shown in FIGS. 7 A-7C wherein the base of the medical device is removed in accordance with an exemplary embodiment.
Figure 8B:
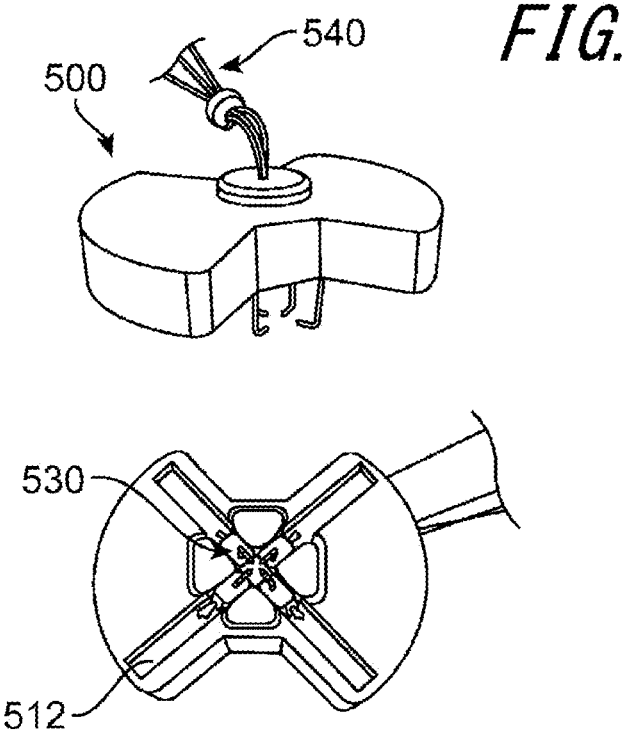
FIG. 8B is a perspective view of the medical device as shown in FIGS. 7 A-7C wherein the base of the medical device is removed in accordance with an exemplary embodiment.
Figure 8C:
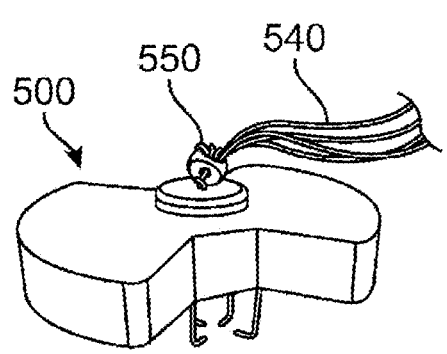
FIG. 8C is a perspective view of the medical device as shown in FIGS. 7 A-7C wherein the base of the medical device is removed in accordance with an exemplary embodiment.
Figure 8D:
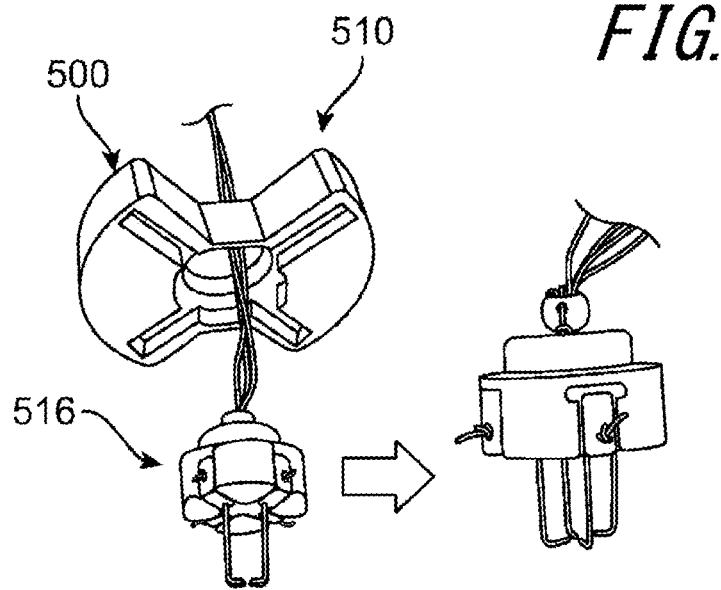
FIG. 8D is a perspective view of the medical device as shown in FIGS. 7 A-7C wherein the base of the medical device is removed in accordance with an exemplary embodiment.

FIGS. 8A-8D are perspective views of the medical device 500 as shown in FIGS. 7A-7C wherein a center portion 516 the base 510 of the medical device is removed in accordance with an exemplary embodiment. As shown in FIG. 8A, the plurality of needles 520 and corresponding levers 530 are set in the base 510 of the medical device 500. In accordance with an exemplary embodiment, a plurality of sutures 540 with a locking feature or locking element 550 can be attached or fixed to an inner portion 532 of each of the levers 530. For example, in accordance with an exemplary embodiment, the locking feature or locking element 550 can be any suitable fastener, such as a spring load fastener. As shown in FIG. 8B, the plurality of sutures 540 are pulled, which causes each of the levers 530 to move inward towards a center of the base 510 within the plurality of slots or tracks 512. As shown in FIG. 8C, the locking feature or locking element 550 in which the plurality of sutures 540 extend through is moved downward onto the base 510 and locks the plurality of levers 530 and corresponding needles 520 in place. As shown in FIG. 8D, the center portion 516 of the base 510 can then be removed from the base 510.

Figure 9A:
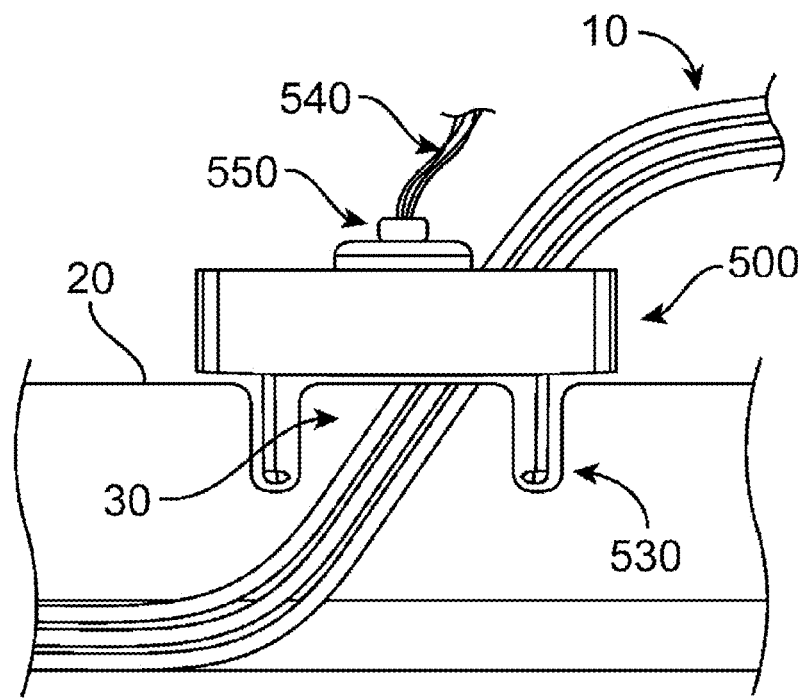
FIG. 9A is a perspective view of the medical device as shown in FIGS. 8A-8D in use with at least one sheath, catheter or the like in accordance with an exemplary embodiment.
Figure 9B:
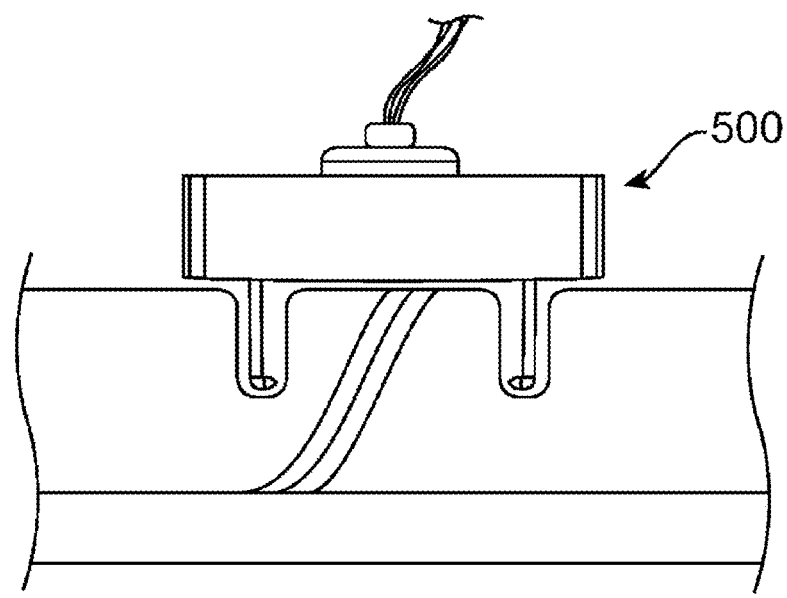
FIG. 9B is a perspective view of the medical device as shown in FIGS. 8A-8D in use with at least one sheath, catheter or the like in accordance with an exemplary embodiment.
Figure 9C:
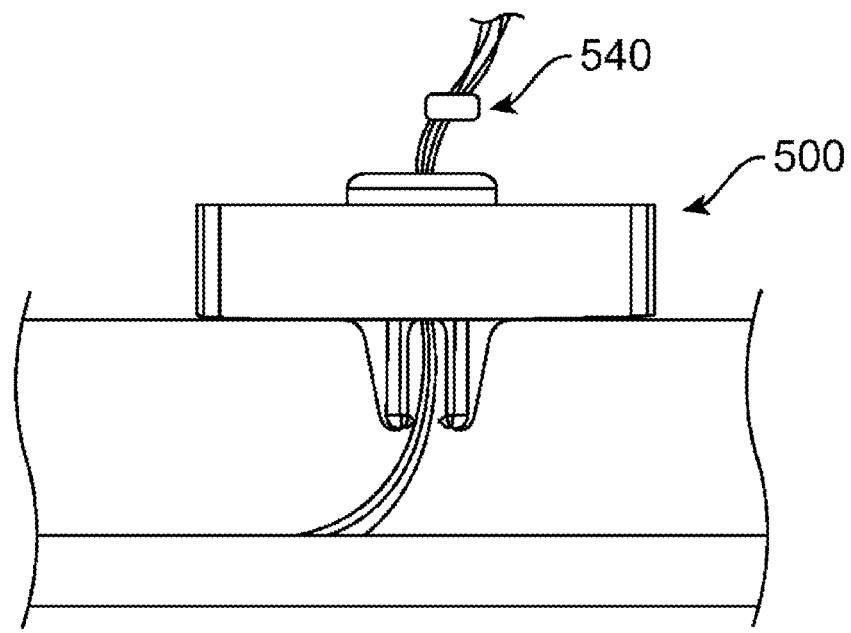
FIG. 9C is a perspective view of the medical device as shown in FIGS. 8A-8D in use with at least one sheath, catheter or the like in accordance with an exemplary embodiment.
Figure 9D:
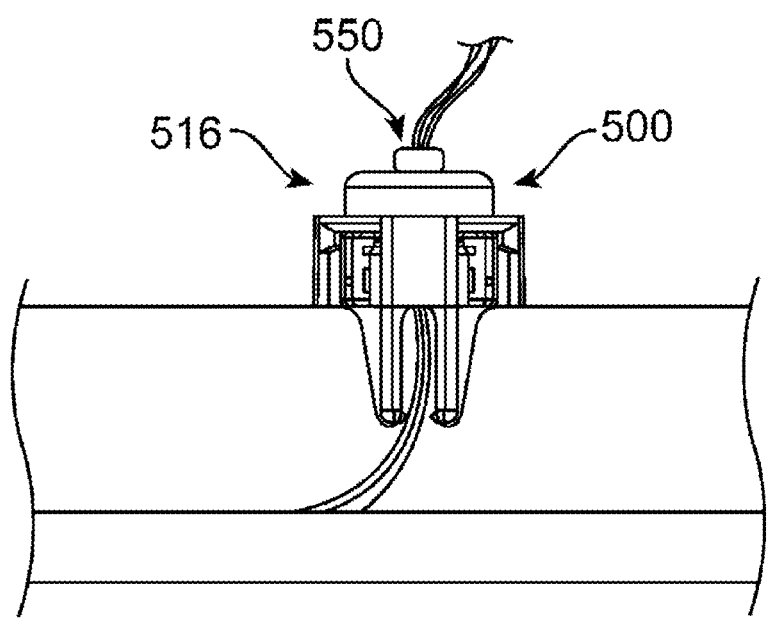
FIG. 9D is a perspective view of the medical device as shown in FIGS. 8A-8D in use with at least one sheath, catheter or the like in accordance with an exemplary embodiment.
Figure 10A:
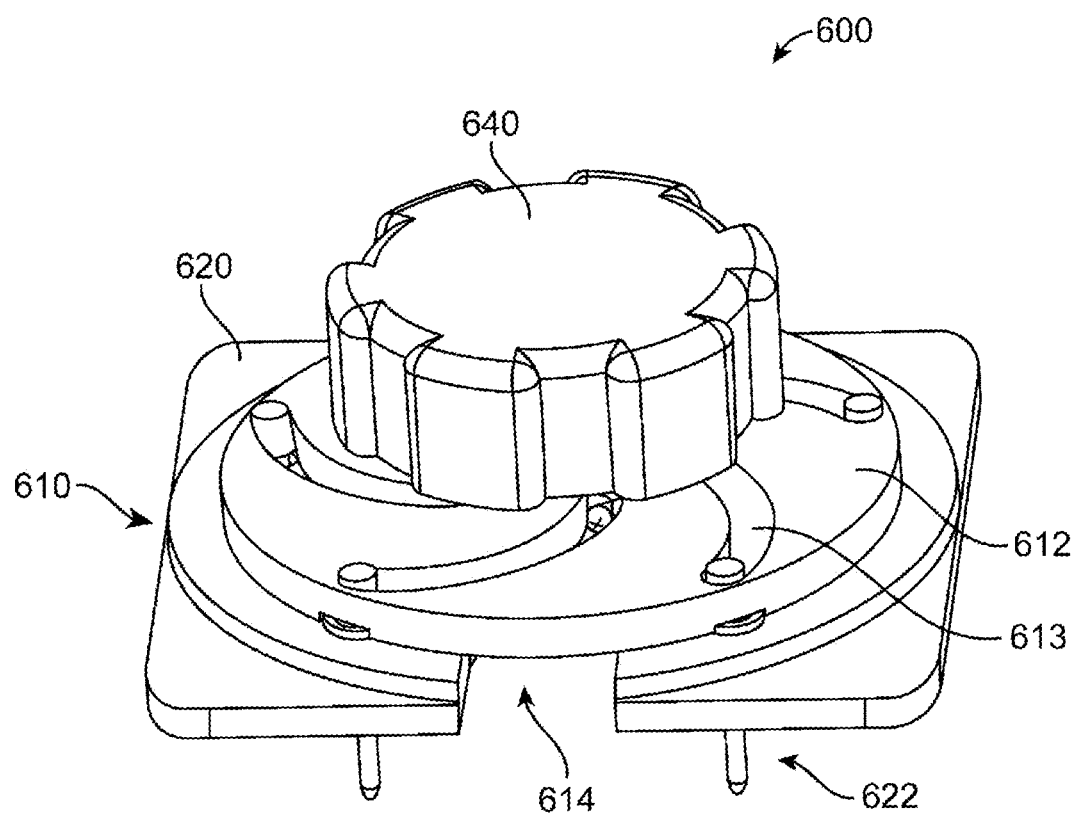
FIG. 10A is a perspective view of a medical device for hemostasis in accordance with an exemplary embodiment.
Figure 10B:
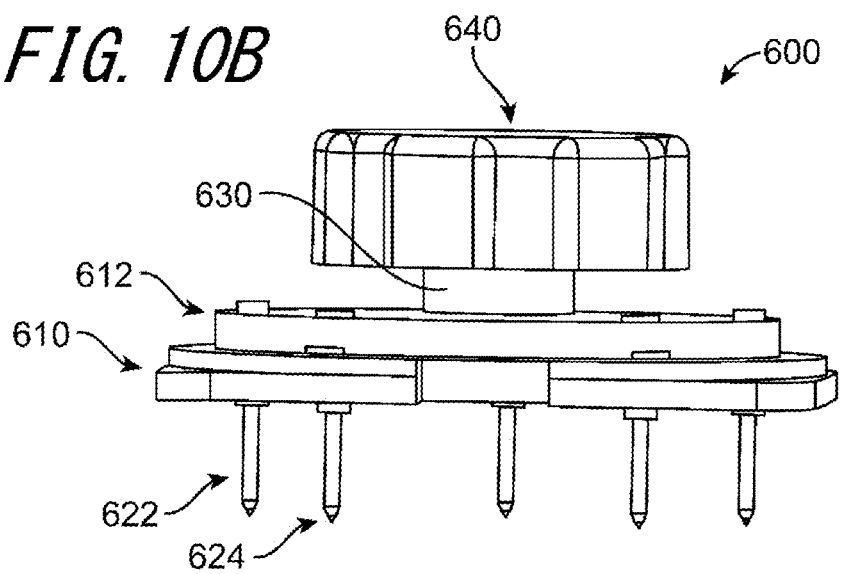
FIG. 10B is a side view of the medical device of FIG. 10A in accordance with an exemplary embodiment.
Figure 10C:
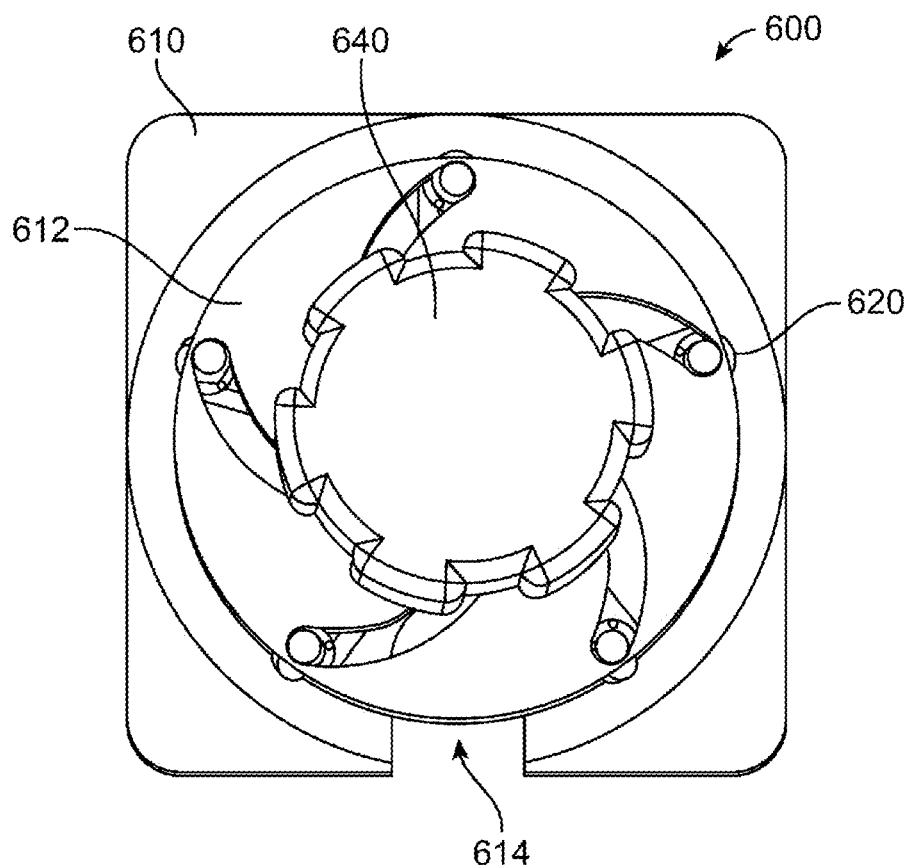
FIG. 10C is a top view of the medical device of FIG. 10A in accordance with an exemplary embodiment.
Figure 10D:
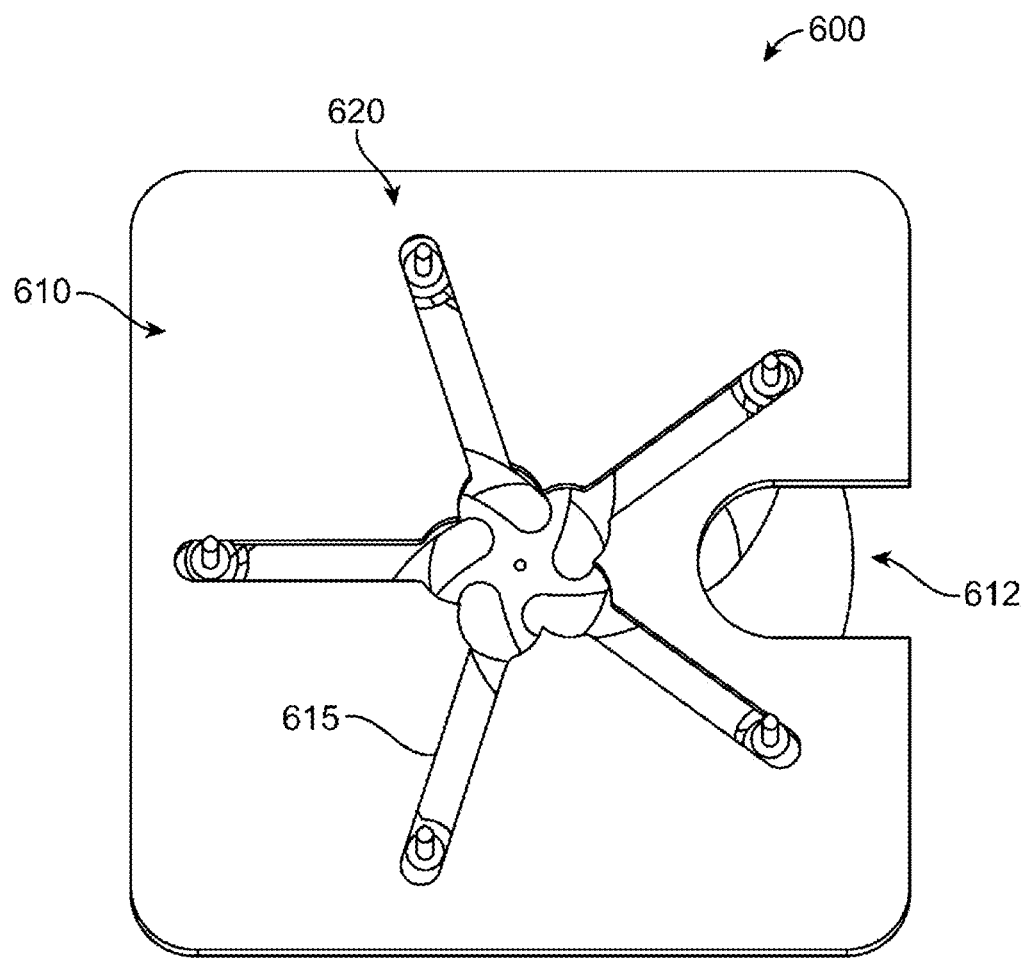
FIG. 10D is a bottom view of the medical device of FIG. 10A in accordance with an exemplary embodiment.

FIGS. 9A-9D are perspective view of the medical device 500 as shown in FIGS. 8A-8D in use with at least one sheath and/or catheter 10 in accordance with an exemplary embodiment. As shown in FIG. 9A, the medical device 500 is placed on the skin 20 of a patient and over the access site 30. In accordance with an exemplary embodiment, the at least one sheath and/or catheter 10 passes through the medical device 500, for example, through the one or more openings or wedges 514. As shown in FIG. 9B, the at least one sheath and/or catheter 10 is removed from the access site 30. As shown in FIG. 9C, the plurality of sutures 540 are pulled, which compresses the plurality of needles 530 inward. As shown in FIG. 9D, the locking feature or locking element 550 is moved downward onto the base 510 and locks the plurality of levers 530 and corresponding needles 520 in place and the center portion 516 of the base 510 can then be removed from the base 510.

FIGS. 10A-10D illustrate a medical device for hemostasis in accordance with an exemplary embodiment. As shown in FIGS. 10A-10D, the medical device 600 includes a base plate 610, a plurality of carrier pins 620, each of the plurality of carrier pins 620 having a needle 622 attached thereto, a grooved plate 612, which upon turning a central knob 640 causes the plurality of carrier pin 602 and needles 622 to move towards the center of the base plate 610. The base plate 610 can also include a cutout 614, which allow sheaths, catheters, and the like to pass through the medical device 600. In accordance with an exemplary embodiment, when the knob 640 is turned clockwise, each curved groove 613 on the plate 612 serves as a slot cam to drive each of the plurality of carrier pins 620 and the needles 622 associated therewith inward along the radial groove 615 on the base plate 610. In accordance with an exemplary embodiment, before the carrier pins 620 and needles 622 are locked in place, turning the knob 640 counterclockwise can reverse the direction of the carrier pins 620 and the needles 622.

In accordance with an exemplary embodiment, each of the plurality of needles 622 preferably extends about 5 mm to 20 mm below a lower surface of the base plate 610. In accordance with an exemplary embodiment, each of the plurality of needles 622 can have a straight tip or an angled tip 624 as disclosed above, which points inward towards a center of the medical device 600. In accordance with an exemplary embodiment, the number of needles 622 is 3 to 8, and more preferably 4. In accordance with an exemplary embodiment, when the needles 622 are in their fully opened configuration, the distance between the center of the knob 640 and each tip 624 should be 10 mm to 20 mm. When the needles 622 are in the fully closed position, the distance between the center of the knob 640 and each tip 624 should be 0.5 mm to 5 mm.

In accordance with an exemplary, the plurality of needles (or subdermal components) 622 are configured to gain traction in the tissue or skin, provide compression, and maintain a relative position until hemostasis is achieved. For example, the carrier pins 620 may be configured in a way such that they all lock against each other when they come to the center of the plate. In accordance with an alternative embodiment, each radial groove 615 on the base plate 610 may have a snapping feature for the carrier pin 620 to snap into when the carrier pins 620 reaches or is close to the center of the base plate 610.

In accordance with an exemplary embodiment, for example, the needles 622 can be small gauge needles, which penetrate the skin, and then apply compression to the wound change. The plurality of needles 622 can be removed after hemostasis is achieved and the wound no longer will bleed.

Figure 11A:
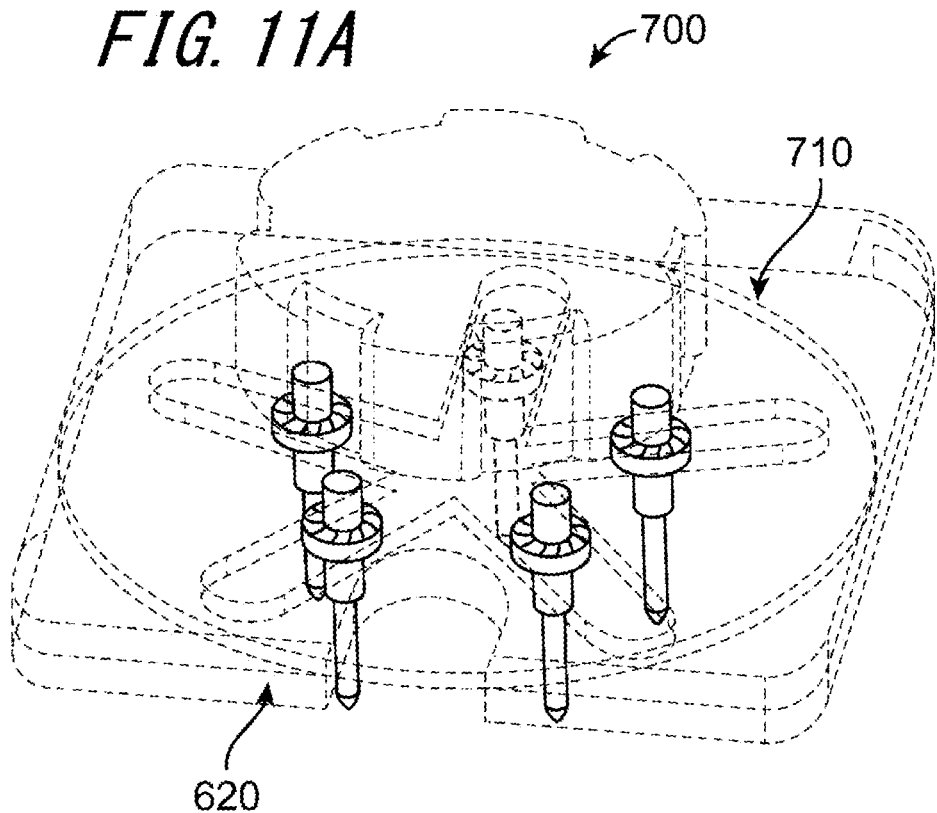
FIG. 11A is a perspective view of a medical device, which is similar to the devices as shown in FIGS. 10A-10D illustrating movement of the needles during use, and which includes a housing.
Figure 11B:
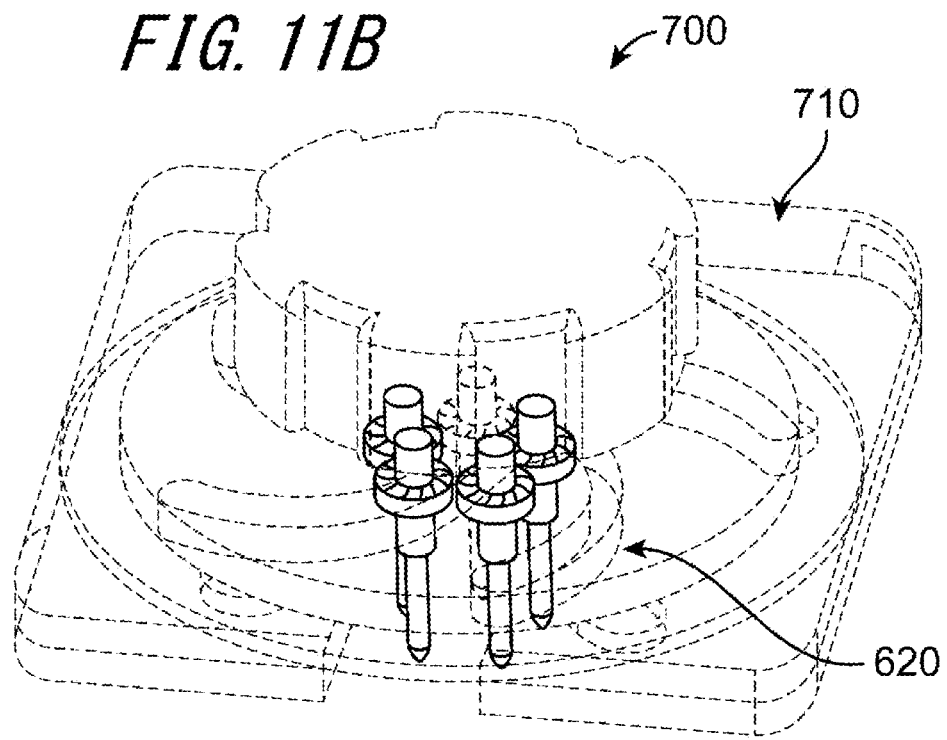
FIG. 11B is a perspective view of a medical device, which is similar to the devices as shown in FIGS. 10A-10D illustrating movement of the needles during use, and which includes a housing.

FIGS. 11A and 11B are perspective view of a medical device 700, which is similar to the devices as shown in FIGS. 10A-10D illustrating movement of the needles 622 during use, and which includes a housing 710. As shown in FIGS. 11A and 11B, upon rotating the central knob, each of the needles move from an outer edge inward towards the center of the medical device 700 within the housing 710.

Figure 12:
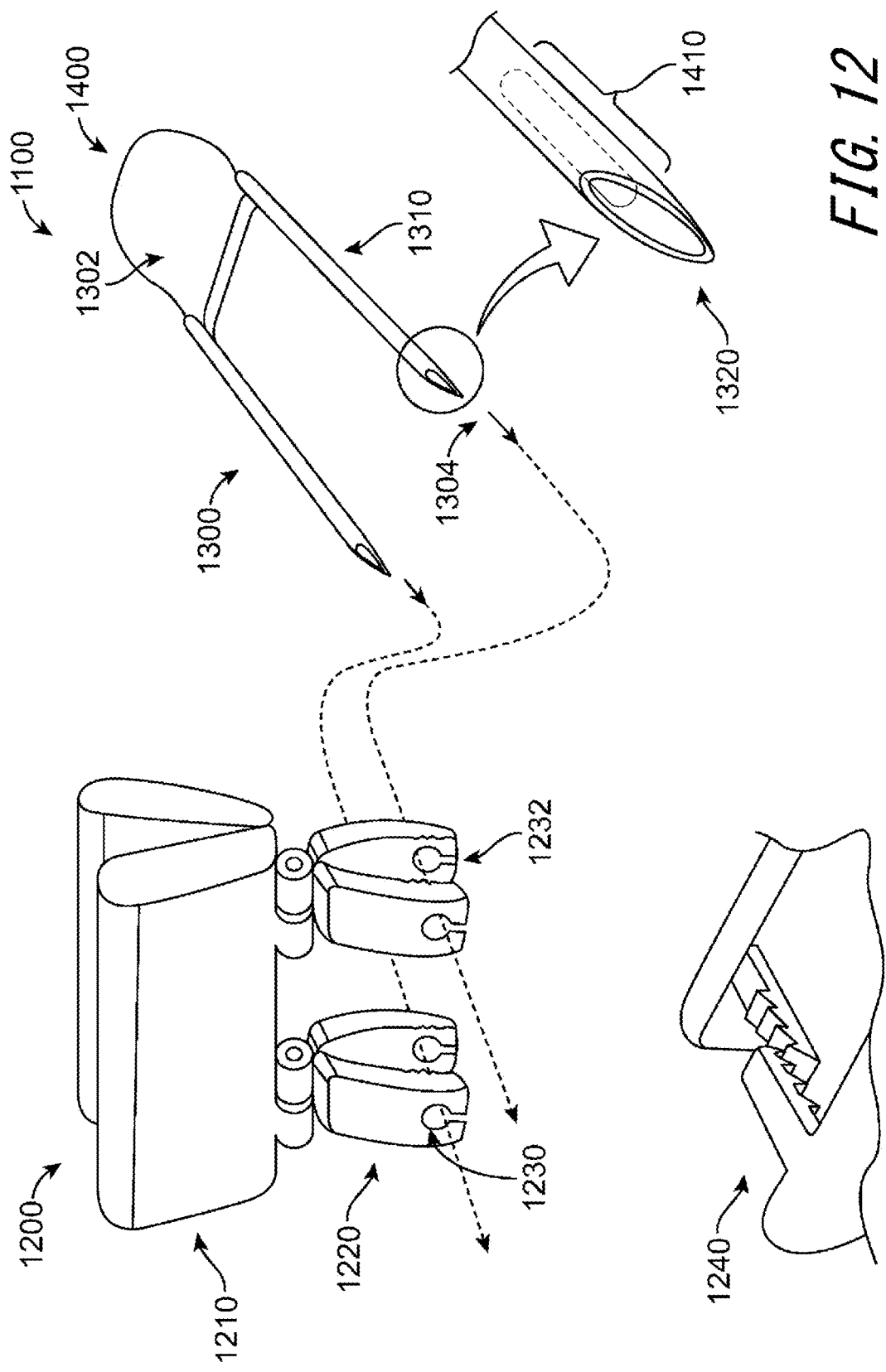
FIG. 12 is a schematic view of a medical device for hemostasis in accordance with an exemplary embodiment.

FIG. 12 is a schematic view of a medical device 1100 for hemostasis in accordance with an exemplary embodiment. As shown in FIG. 12, the medical device 100 can be configured to emulate the mechanism of the figure-of-eight suturing in which the tissue surrounding the puncture site between the vein and the skin is compressed to achieve hemostasis. In accordance with an exemplary embodiment, the medical device (or clip) 1100 can include a pinching device (or clip) 1200, a needle 1300, and a suture 1400. The pinching device (or clip) 1200 can include a pair of actuating grips 1210, a pair of pinching jaws 1220, a pinching jaw hole 1230 in each of the pair of pinching jaws 1220, and a pinching jaw slot 1232 in each of the pair of pinching jaws 1220. The pinching jaw holes 1230 form a needle guide. In accordance with an exemplary embodiment, the pair of actuating grips 1210 may each have a locking ratchet 1240 for example, like that of a hemostat, which locks the pair of actuating grips 1210 to one another.

In use, in order to improve safety, the medical device 1100 as disclosed herein can be arranged on the tissue or skin such that upon closing of the pinching jaws 1220 of the medical device 1100, for example, the pinching jaws 1220 can be arranged either parallel or perpendicular to the blood vessel. In addition, the blood vessel is not pinched, but rather the tissue or skin above the blood vessel is pinched by the medical devices 1200, 2100, 2200 as disclosed herein. In addition, based on a length of each of the pinching jaws 1220, a depth and a width of tissue being pinched can be controlled. In accordance with an exemplary embodiment, each of the pinching devices (or clips) 1200, 2100, and 2200 are configured to pinch the tissue of the living body above the blood vessel. In addition, each of pinching devices (or clips) 1200, 2100, 2200 can be arranged either parallel or perpendicular to the blood vessel.

The needle 1300 preferably includes a pair of spaced apart hollow needles 1310, which are connected at a proximal end 1302 and configured to receive the suture 1400. As shown in FIG. 12, the proximal end 1302 and the distal end 304 are open to receive the suture 1400. Each of the pair of spaced apart needles 1310 on a distal end 1304 has an angled tip 1320. The suture 1400 is configured to be received in the hollow portion of the pair of spaced apart hollow needles 1310 and has a pair of anchors 1410, for example, T-bar anchors on each end of the suture 1400.

Figure 13:
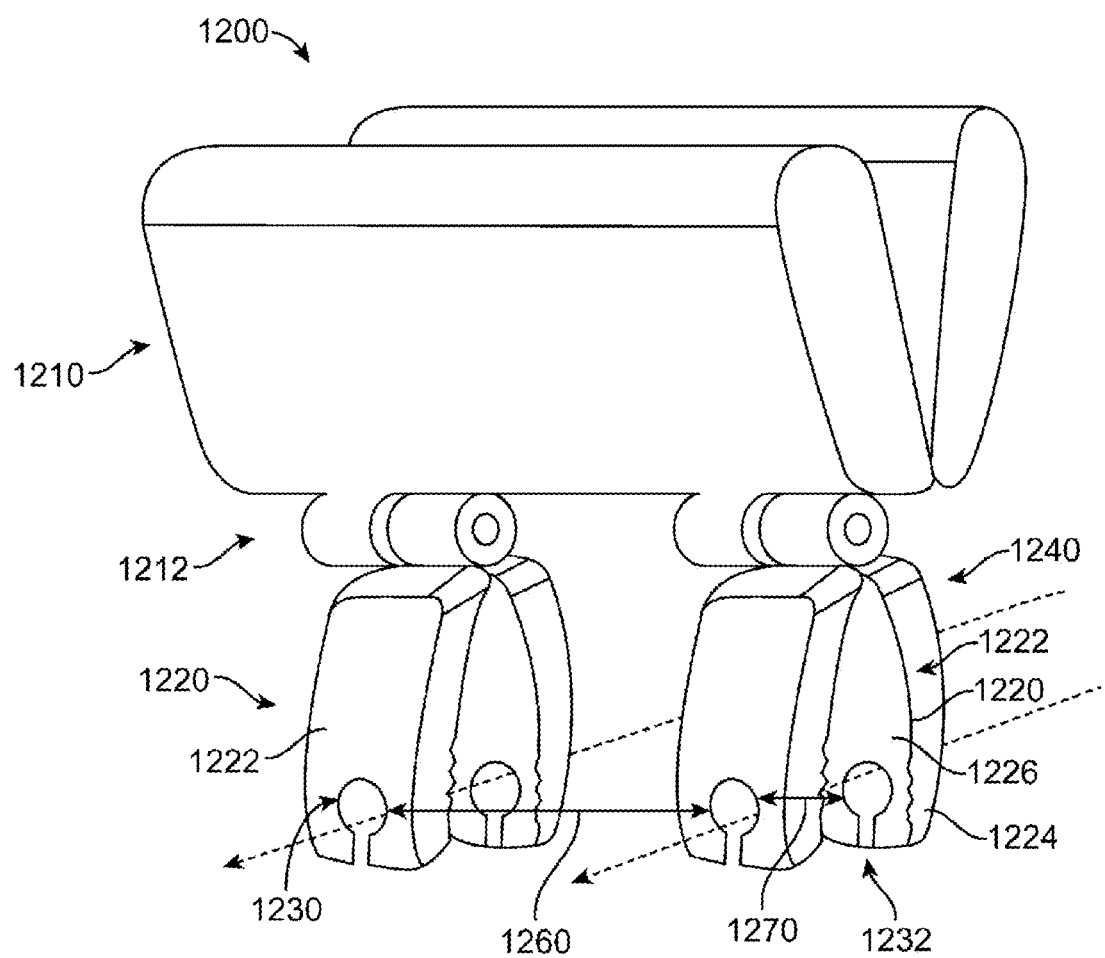
FIG. 13 is a perspective view of a pinching device or clip of the medical device as shown in FIG. 12 in accordance with an exemplary embodiment.

FIG. 13 is a perspective view of a pinching device or clip 1200 of the medical device as shown in FIG. 12 in accordance with an exemplary embodiment. As shown in FIG. 13, the pinching device (or clip) 1200 can include a pair of actuating grips 1210, a pair of pinching jaws 1220, a pinching jaw hole 1230 in each of the pair of pinching jaws 1220, and a pinching jaw slot 1232 in each of the pair of pinching jaws 1220. In accordance with an exemplary embodiment, a distance 1260 between each pair of the pinching jaw holes 1230, 1232, may be 20 mm to 40 mm. In addition, a distance 1270 between the pinching jaw holes 1230, 1232 for each pair of pinching jaws 1220 when in an open position may be 20 mm to 40 mm. In addition, a gap 1240 exists between a lower edge of the actuating grips 1210 and an upper edge of the pair of pinching jaws 1220 such that medical sheaths, catheters, and the like can pass through the pinching device 1200 such that the pinching device 1200 can be placed over the inserted sheaths, catheters, and the like.

In accordance with an exemplary embodiment, the pair of actuating grips 1210 can be generally rectangular plates or panels, having a spring operated or spring-like hinge 1212, which connects a bottom side of each of the pair of actuating grips 1210 to each jaw 1222 of the pair of pinching jaws 1220. As shown, the pinching device or clip 1200 has four jaws 1222. On an inner portion 1226 of each of the jaws 1222, the surface 1224 can be relatively smooth, or alternatively, can have ridges or an irregular surface or pattern to provide a surface on the jaw 1222, which can grip the skin of the living body.

FIG. 14A is a perspective view of a needle 1300 of the medical device 1100 as shown in FIG. 12 in accordance with an exemplary embodiment. As shown in FIG. 14A, the needle 1300 preferably includes a pair of spaced apart hollow needles 1310, which are connected a proximal end 1302 and configured to receive the suture 1400. Each needle 1312, 1314 of the spaced apart hollow needles 1310 are hollow and configured to receive a suture 1400 having an anchor, for example, a T-bar anchor on each end of the suture 1400. The pair of spaced apart hollow needles 1310 have a connector 1330 on the proximal end 1302, which can be connected to a handle (or grip) 1340, which can be used to push the pair of spaced apart hollow needles 1310 through the skin during use. In accordance with an exemplary embodiment, the handle (or grip) 1340 can be round cylinder having a plurality of ridges 1342 to assistant an operator in gripping the handle 1340. The handle 1340 can also be flat or any other shape, which a user can relatively easily grip and help assistant the user in pushing the pair of spaced apart needles 1310. As shown in FIG. 14A, on the distal end 1304 of each of the pair of spaced apart hollow needles 1310, the distal end 1304 can be cut at an angle 1322 to form a sharp point 1320. In accordance with an exemplary embodiment, the needle 1300 is preferably stainless steel.

FIG. 14B is another perspective view of a needle 1300 with a suture 1400 for use with the medical device as shown in FIG. 12 in accordance with an exemplary embodiment. As shown in FIG. 14B, the pair of spaced apart hollow needles 1310 are configured to receive a suture 1400 having a pair of anchors 1410 on each end 1412, 1414 of the suture 1400.

FIG. 15 is a perspective view of a needle 1300 for use with the medical device as shown in FIG. 12 in accordance with an exemplary embodiment. As shown in FIG. 15, the needle 1300 can include a pair of spaced apart needles 1310 having a slot 1316 on an upper surface (or spine) 1318, which allows the suture 1400 to escape or be removed from each of the spaced apart needles 1312, 1314, when the needles 1310 are removed from the skin of the living body.

In accordance with an exemplary embodiment, the medical device 1100 can also include a pusher 1360, which can be used to push or eject the anchor 1410 of the suture 1400. The pusher 1360 can be a U-shaped bar having a pair of ends 1362, 1364, having a relatively flat surface, which can be used to eject or push the suture 1400 out of the distal end 1304 of the pair of spaced apart needles 1310.

FIG. 16 is an illustration of a use of the medical device 1100 for hemostasis in accordance with an exemplary embodiment. As shown in FIG. 16, in step 1510, the pinching jaws 1220 of the pinching device (or clip) 1200 pinch or grab the skin of the living body. In step 1520, the actuating grips 1210 are locked in place using, for example, the locking ratchet or other locking means and the pair of spaced apart needles 1210 is pushed through the pinching jaw holes 1230 and tissue of the living body. In step 1530, the pusher 1360 pushes the suture 1400 and the anchors 1410 out the distal ends 1304 of the pair of spaced apart needles 1310. In step 1540, the actuating grips 1210 and the pair of pinching jaws 1230 are removed from the tissue or skin where the pair of spaced apart needles 1210 pierce the skin. In accordance with an exemplary embodiment, the suture 1400 is allowed to be removed from the pair of spaced apart needles 1210 through the slot 1316 (FIG. 15) in the spine 1318 of each of the hollow needles 1312, 1314. In step 1550, a one-way collar 1560 may be fed over a proximal end of the suture 1400 and cinched to tighten the suture 1400.

FIG. 17 is a perspective view of a hemostatic pin 1600 in accordance with an exemplary embodiment. In accordance with an exemplary embodiment, instead of the needle 1300, the suture 1400, and the pusher 1360 as disclosed above, the pinching device (or clip) 1200 can be used with a hemostatic pin 1600, for example as shown in FIGS. 17 and 19A-19D. As shown in FIG. 17, the hemostatic pin 1600 can include a pair of distal tips 1610, 1612, a main body 1620 comprising a pair of spaced apart members 1630, 1632, which converge on a proximal end 1640. On a proximal portion 1650, the hemostatic pin 1600 includes a cinching portion 1660. In accordance with an exemplary embodiment, the distance between the pair of distal tips 1610, 1612 may be 20 mm to 40 mm. In addition, a gap 1662 at the cinching portion 1660 may be 1 mm to 10 mm.

Figure 18:
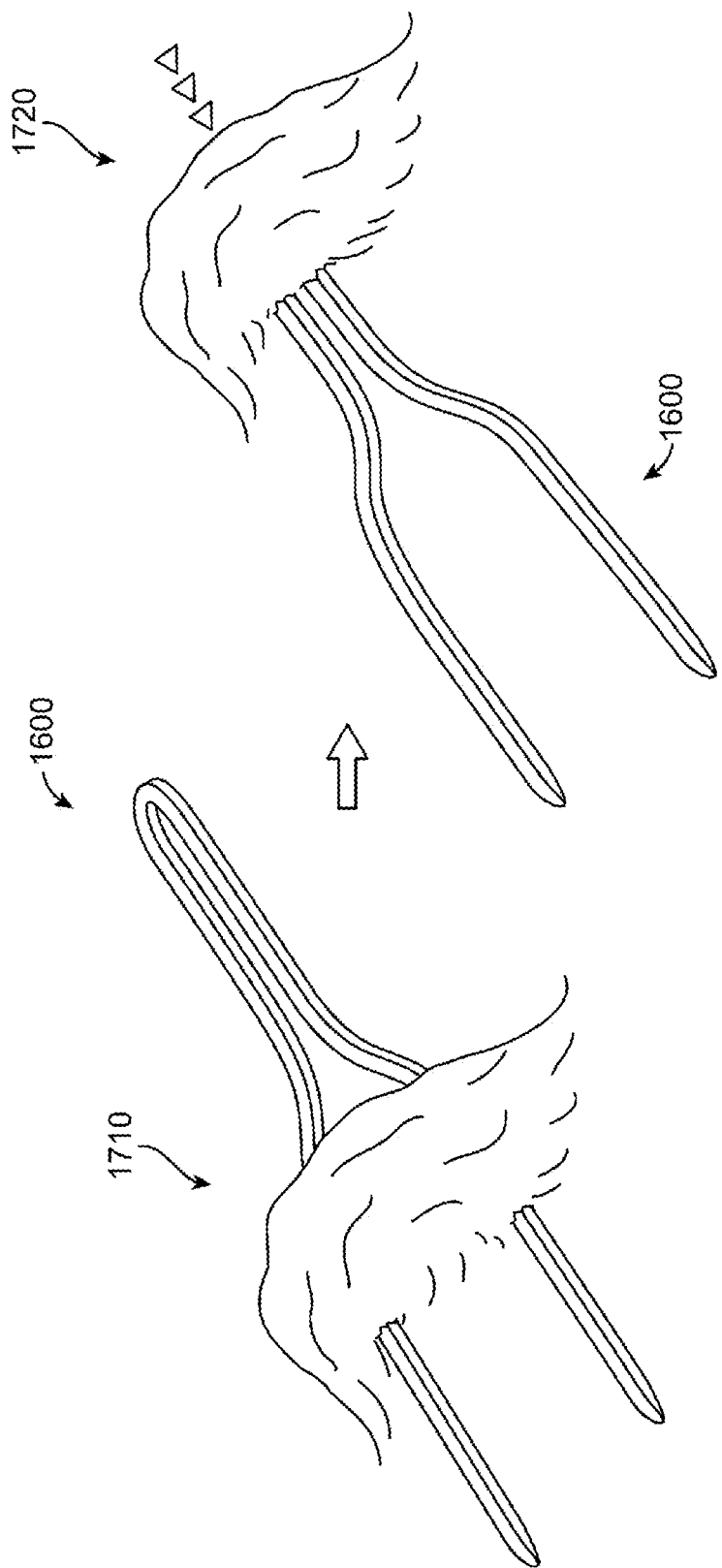
FIG. 18 is an illustration of a use of the hemostatic pin for hemostasis in accordance with an exemplary embodiment.

FIG. 18 is an illustration of a use of the hemostatic pin 1600 for hemostasis in accordance with an exemplary embodiment. As shown in FIG. 18, in step 1710, the pinching device (or clip) 1200 cinches or pinches the tissue of the living body, and the distal tips 1610, 1612 of the hemostatic pin 1600 are pushed through the skin. In accordance with an exemplary embodiment, the distal tips 1610, 1612 of the hemostatic pin 1600 are preferably sharp enough to be pushed through the skin with relatively little or no pain when left in the tissue of the living body or patient. In step 1720, the hemostatic pin 1600 is pushed (or advanced) through the tissue (or skin) to create a cinch in the tissue (skin).

Figure 19A:
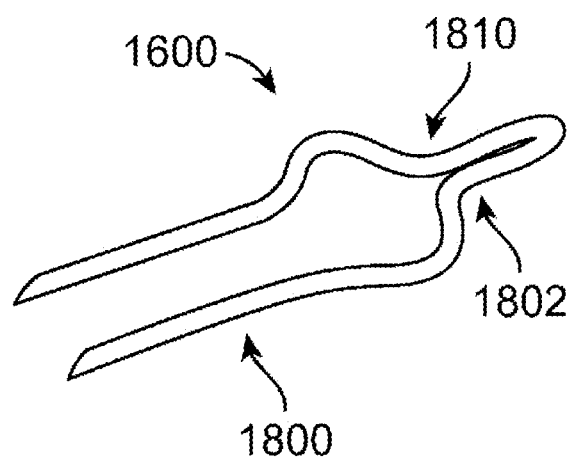
FIG. 19A is a perspective view of hemostatic pins in accordance with an exemplary embodiment.
Figure 19B:
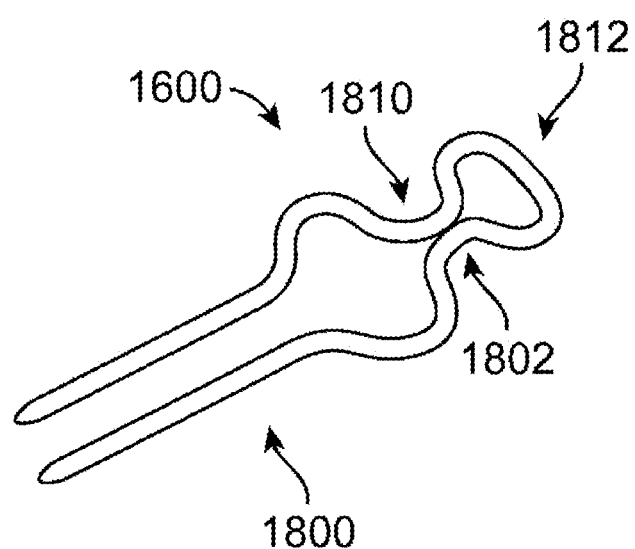
FIG. 19B is a perspective view of hemostatic pins in accordance with an exemplary embodiment.
Figure 19C:
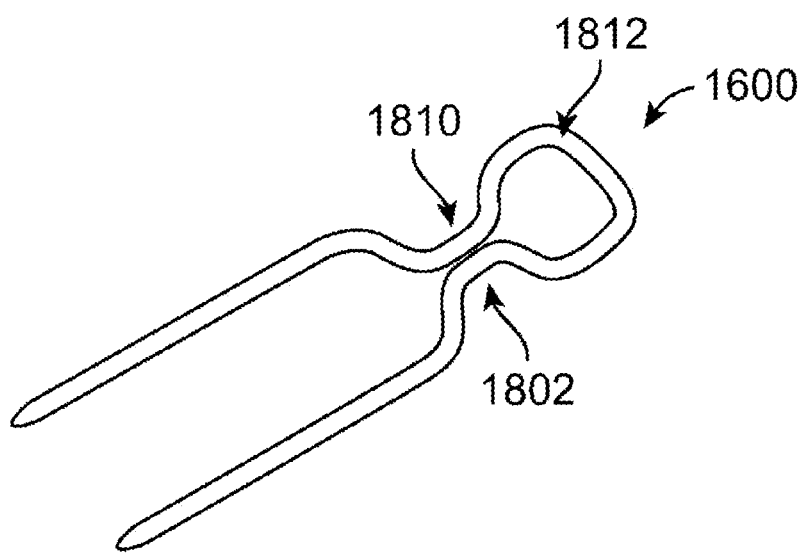
FIG. 19C is a perspective view of hemostatic pins in accordance with an exemplary embodiment.

FIGS. 19A-19D are perspective view of hemostatic pins 1600 in accordance with an exemplary embodiment. As shown in FIG. 19A, the main body 1620 includes a portion 1800 to the distal side of the cinching portion 1660, which bows outward. In FIG. 19B, the cinching portion 1660 includes a narrow portion 1810 on the distal side and a bowed outward or rounded proximal side 1812. In FIG. 19C, the hemostatic pin 1600 does not include the portion 1800, which bows outward, and includes the cinching portion 1660 includes the narrow portion 1810 on the distal side and the bowed outward or rounded proximal side 1812. In accordance with an exemplary embodiment, for example, as shown in FIGS. 19A-19C, a gap 1802 in the narrow portion 1810 of the cinching portion 1660 can be 1 mm to 10 mm.

Figure 19D:
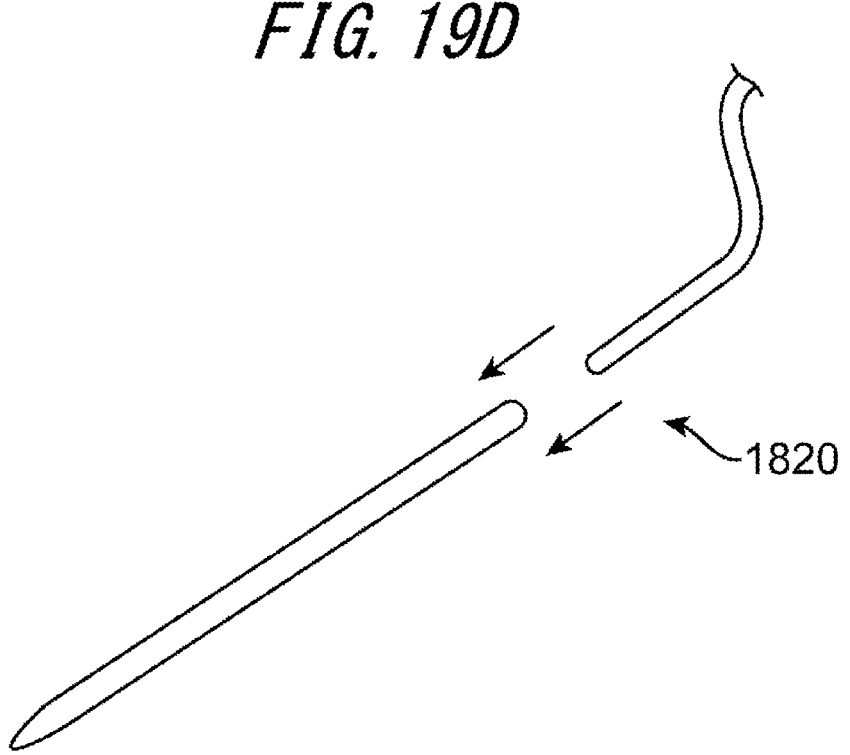
FIG. 19D is a perspective view of hemostatic pins in accordance with an exemplary embodiment.

In accordance with an exemplary embodiment, for example, as shown in FIG. 19D, the distal tips 1610, 1612 can be configured to be separable 1820 from the main body 1620 of the hemostatic pin 1600.

Figure 20A:
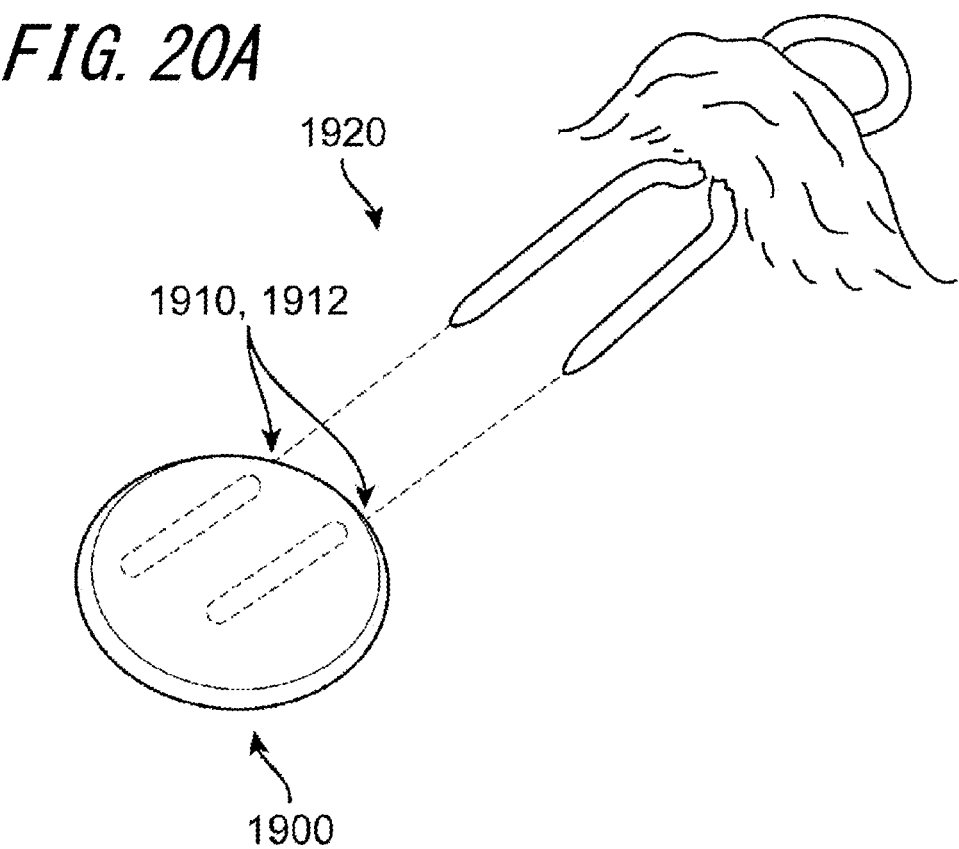
FIG. 20A is an illustration of a use of the hemostatic pin for hemostasis in accordance with an exemplary embodiment.
Figure 20B:
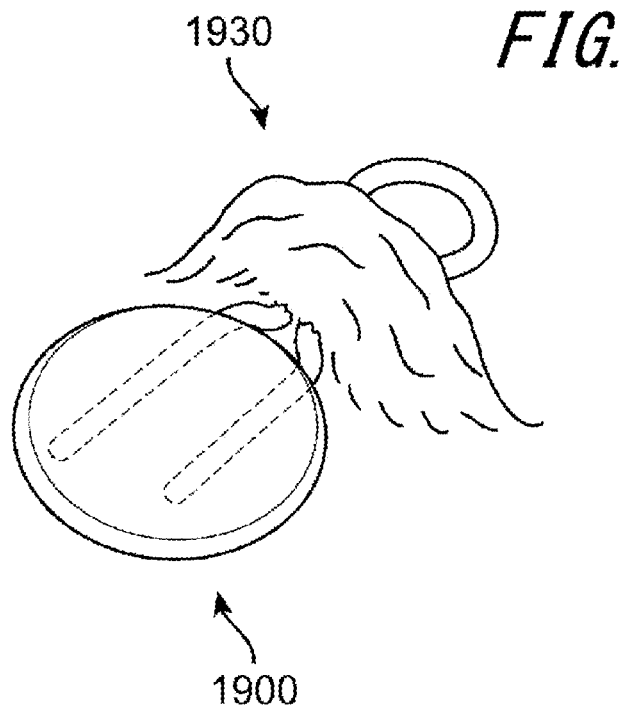
FIG. 20B is an illustration of a use of the hemostatic pin for hemostasis in accordance with an exemplary embodiment.

FIGS. 20A and 20B is an illustration of a use of the hemostatic pin 1600 for hemostasis in accordance with an exemplary embodiment. As shown in FIG. 20A, the hemostatic pins 1600 as disclosed herein can be used with a safety cap 1900, which can help protect the patient from the sharp distal tips 1610, 1612 of the hemostatic pin. In accordance with an exemplary embodiment, the safety cap 1900 can include two holes (or cavities) 1910, 1912, configured to receive the distal tips 1610, 1612 of the hemostatic pin 1600. The safety cap 1900 can be round, rectangular, or any other suitable shape. As shown in FIG. 20B, in step 1920, the hemostatic pin 1600 is pushed through the skin. In step 1930, the safety cap 1900 is placed on the distal ends 1610, 1612 of the hemostatic pin 1600. In accordance with an exemplary embodiment, the safety cap 1900 can be made of plastic or other suitable material.

Figure 21A:
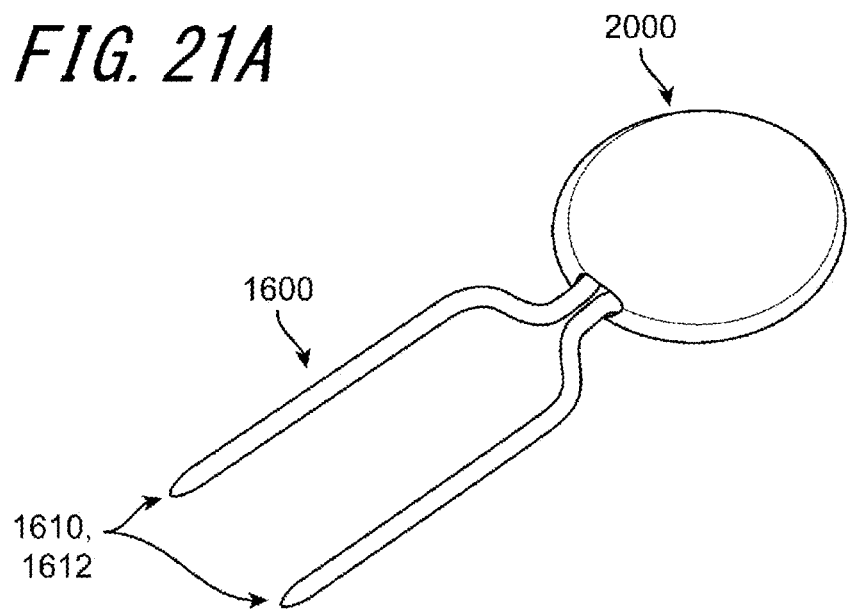
FIG. 21A is an another illustration of a use of the hemostatic pin for hemostasis in accordance with an exemplary embodiment.
Figure 21B:
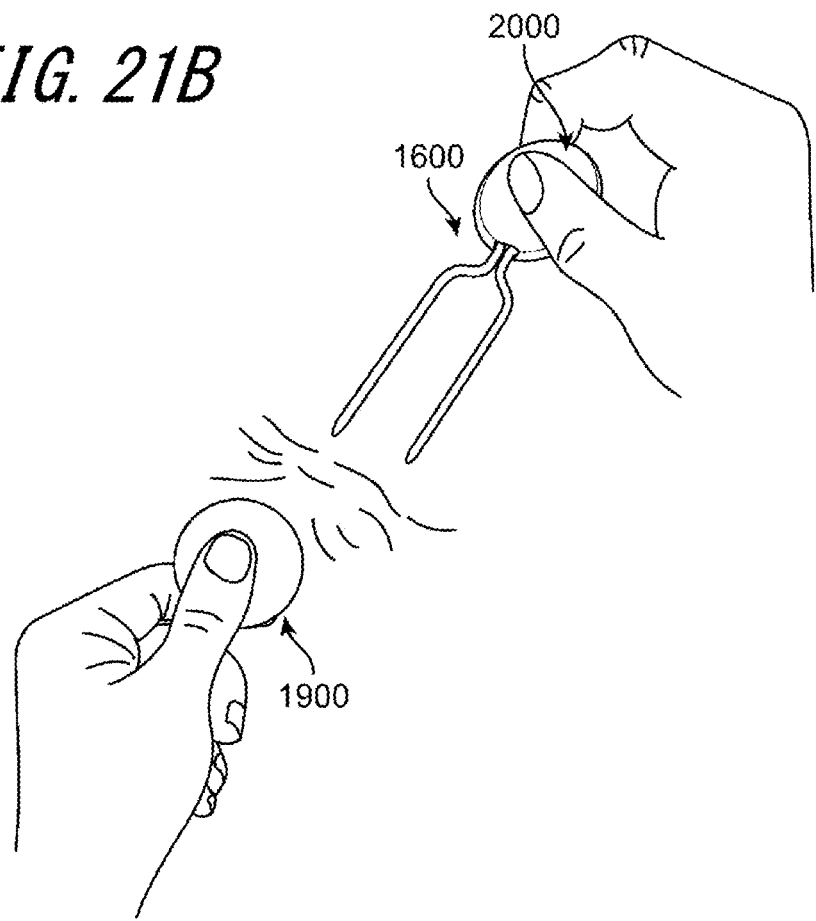
FIG. 21B is an another illustration of a use of the hemostatic pin for hemostasis in accordance with an exemplary embodiment.

FIGS. 21A and 21B are another illustration of a use of the hemostatic pin 1600 for hemostasis in accordance with an exemplary embodiment. As shown in FIG. 21A, the hemostatic pin 1600 can include a gripping portion 2000 on the proximal end to assist the user in inserting the hemostatic pin 1600 through the skin or tissue. In accordance with an exemplary embodiment, the gripping portion 2000 may have the same configuration as the safety cap 1900, or alternatively, a different configuration. In addition, the gripping portion 2000 may also be comprised of a same material as the safety cap 1900, covered by the same material 1900 as the safety cap 1900, or a different material than the safety cap 1900. As shown in FIG. 21B, once hemostasis is achieved, the hemostatic pin 1600 can be easily removed by removing the safety cap 1900 and then pulling on the gripping portion 2000 in a direction away from the tissue (or skin) to remove the hemostatic pin 1600. In accordance with an exemplary embodiment, the safety cap 1900 and the gripping portion 2000 can be made of, for example, polycarbonate, nylon, ABS (Acrylonitrile-Butadiene-Styrene), polyethylene, silicone, polypropylene, PTFE (Polytetrafluoroethylene), etc.

Figure 22:
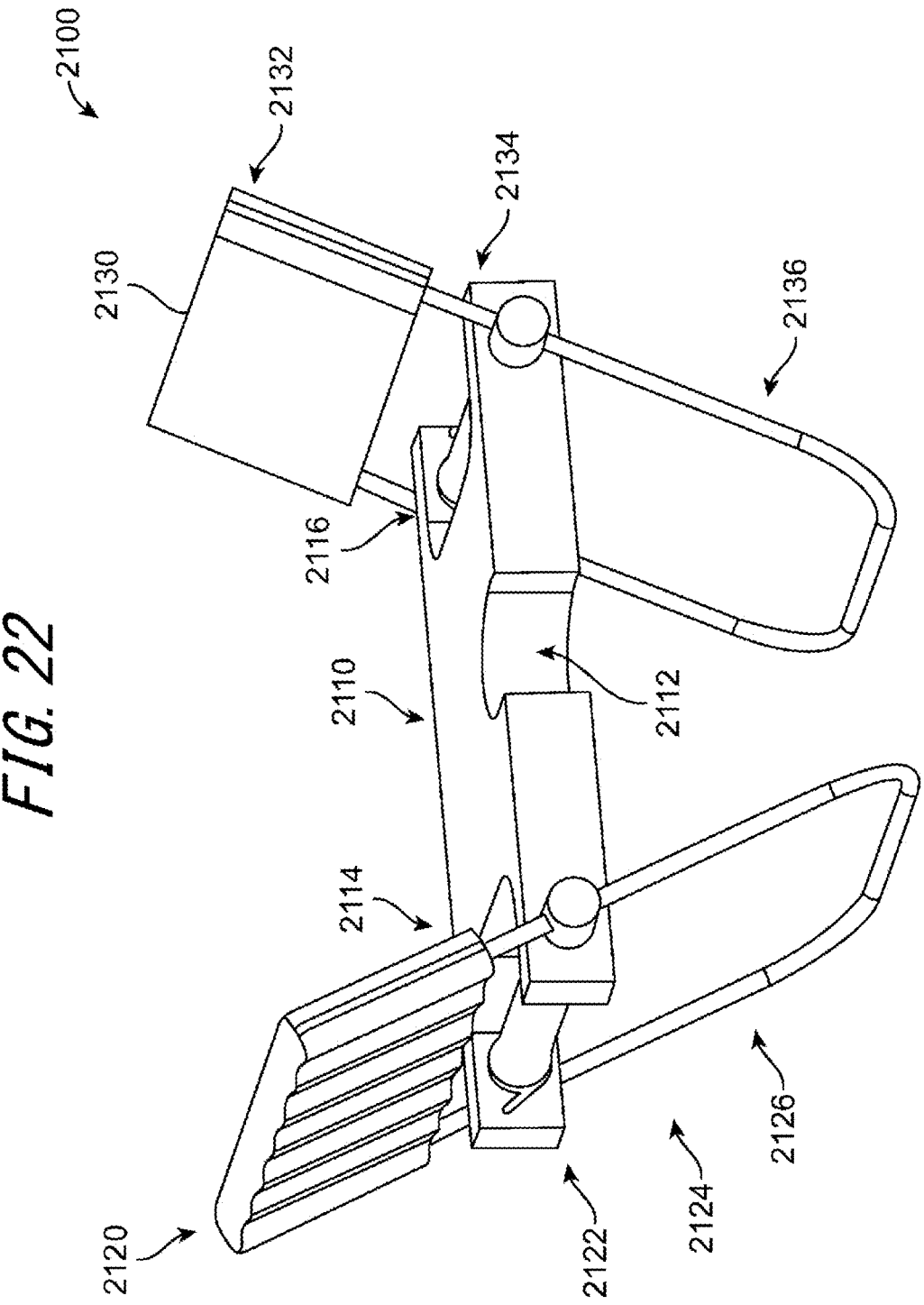
FIG. 22 is a perspective view of a clip for hemostasis in accordance with an exemplary embodiment.
Figure 23A:
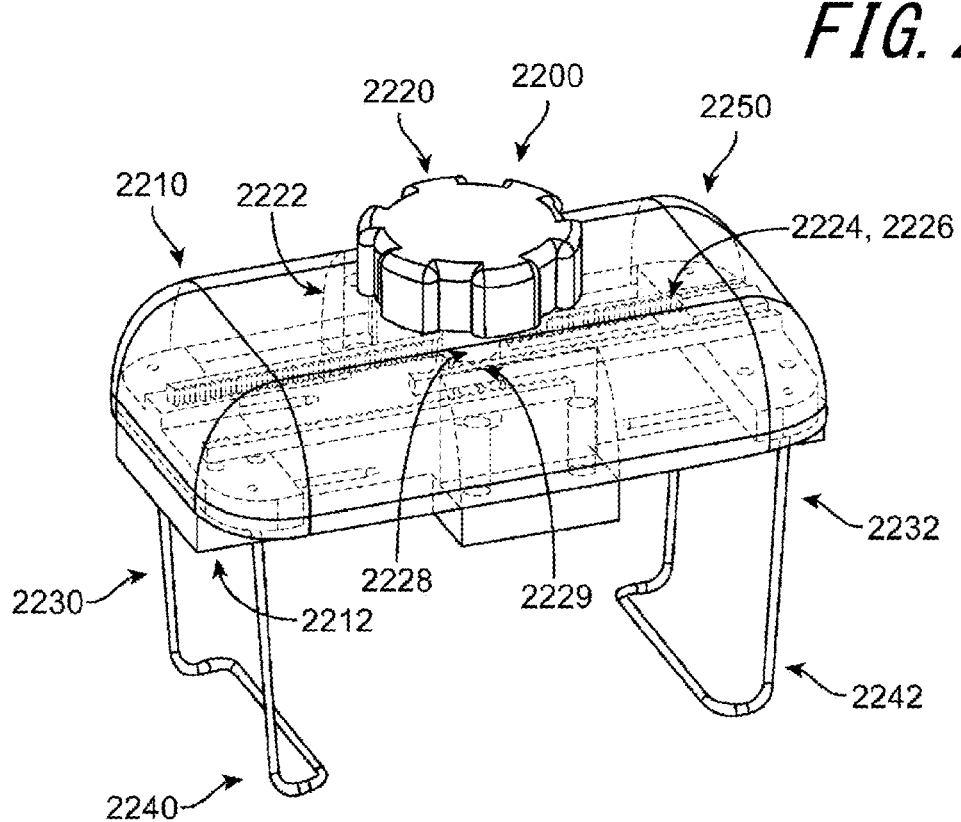
FIG. 23A is a perspective view of a clip for hemostasis in accordance with another exemplary embodiment.
Figure 23B:
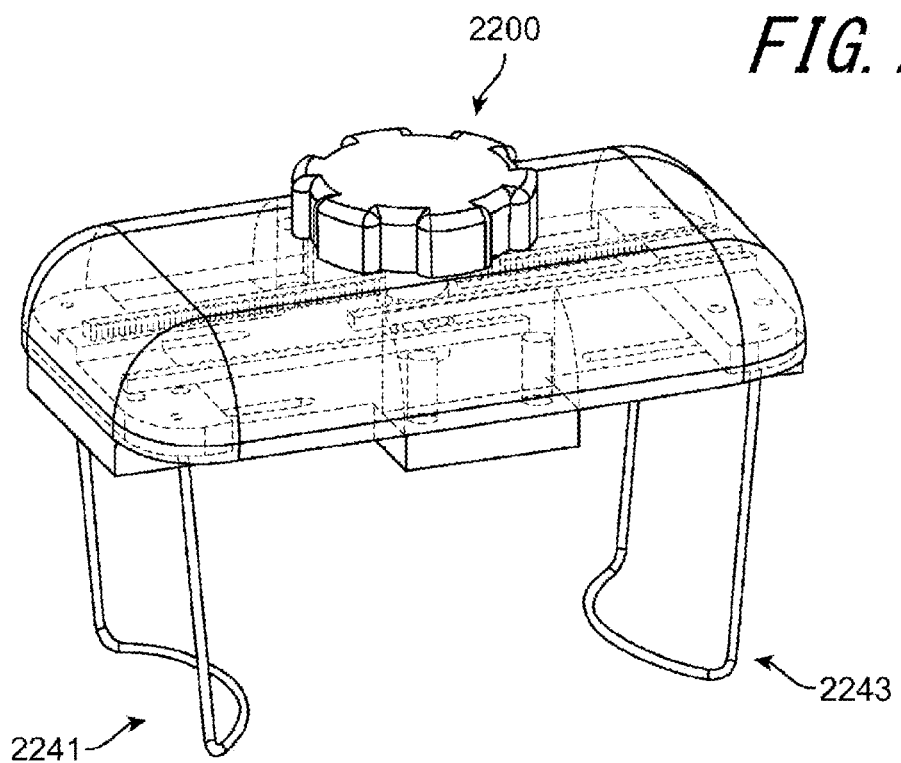
FIG. 23B is a perspective view of a clip for hemostasis in accordance with another exemplary embodiment.
Figure 23C:
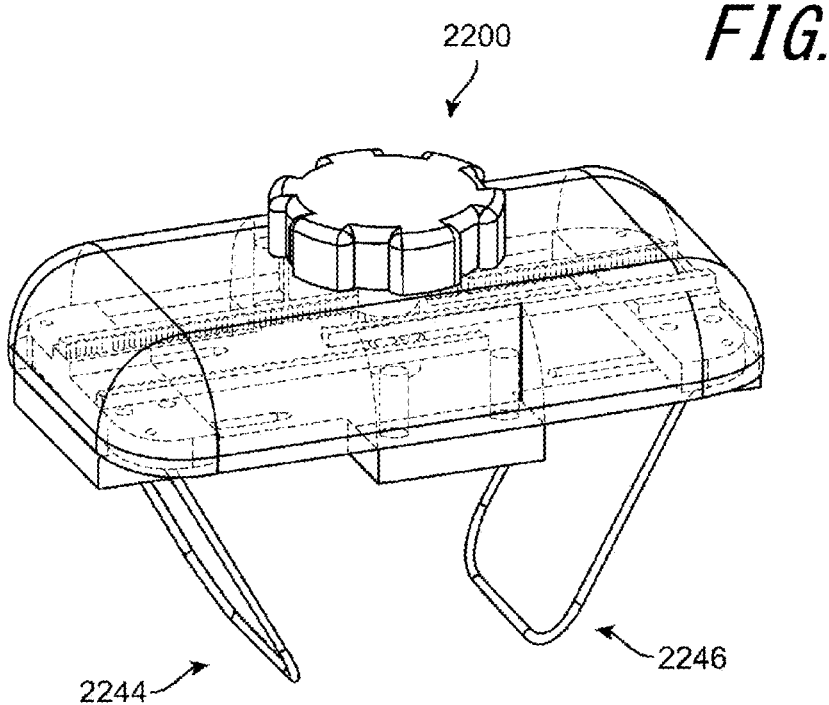
FIG. 23C is a perspective view of a clip for hemostasis in accordance with another exemplary embodiment.
Figure 23D:
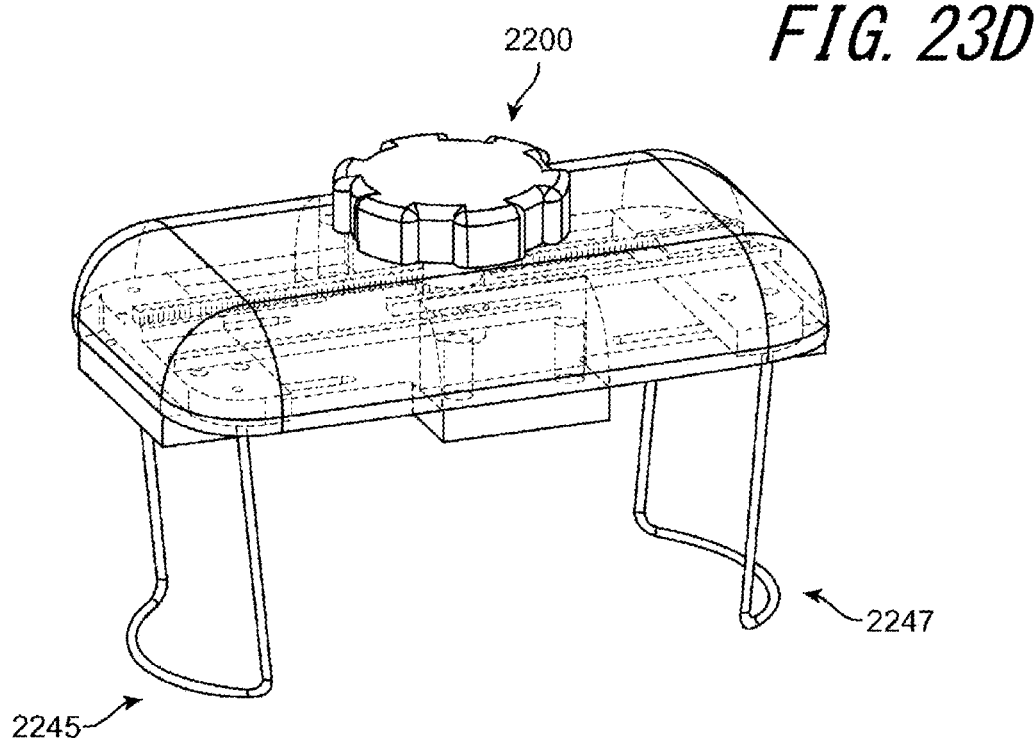
FIG. 23D is a perspective view of a clip for hemostasis in accordance with another exemplary embodiment.

FIG. 22 is a perspective view of a clip 2100 for hemostasis in accordance with an exemplary embodiment. As shown in FIG. 22, the clip 2100 can include a base member 2110, and a pair of a passive spring members 2120, 2130. The base member 2110 includes a front cutout section 2112, and two side cutout sections 2114, 2116. The two side cutout sections 2114, 2116 are configured to receive the passive spring members 2120, 2130. In addition, the front cutout section 2112 can be configured to allow sheaths, catheters, and the like to pass through the clip 2100 and which allows the clip 2100 to be placed over the inserted sheaths, catheters, and the like. Each of the passive spring members 2120, 2130 includes a handle 2122, 2132, a hinged spring member 2124, 2134, and a wire arm 2126, 2136. In accordance with an exemplary embodiment, the wire arms 2126, 2136 are configured to be spring loaded inward and upon pressing (or squeezing) on the handles 2122, 2132, the wire arms 2126, 2136 open. The clip 2100 is configured to placed flat onto the skin, and releasing the wire arms 2126, 2136 to provide compression to create hemostasis.

In accordance with an exemplary embodiment, the base member 2110 can be, for example, approximately 20 mm to 40 mm by approximately 20 mm to 40 mm with the length of the wire arms being, for example, 5 mm to 20 mm in length measured from a lower surface of the base member 2110. In accordance with an exemplary embodiment, the wire arms can be a coated wire or having an abrasive outer surface to help grip the tissue (skin).

FIGS. 23A-23D are perspective view of a clip 2200 for hemostasis in accordance with another exemplary embodiment. As shown in FIGS. 23A-23D, the clip includes a housing member 2210, a central knob 2220, a pair of wire arms 2230, 2232, each of the wire arms 2230, 2232 having a skin-interface member 2240, 2242, and a mechanism 2250 housed in the housing member 2210, which upon turning the central knob 2220, the skin-interface 2240, 2242 compresses the tissue (or skin) to create hemostasis. When the central knob 2220 is turned, in accordance with an exemplary embodiment, a rack-and-pinion system 2222 moves each rack 2224, 2226 in the opposite directions. The central knob 2220 is on a shaft 2228 that is connected to a pinion gear 2229 whose center is coaxial to the shaft 2228. In accordance with an exemplary embodiment, two racks 2224, 2226 are placed on opposite sides of the pinion gear 2229 such that when the knob 2220 is turned each rack 2224, 2226 moves in the opposite directions. The end of each rack 2224, 2226 is connected to the respective wire arm (2230, 2232). In accordance with an exemplary embodiment, to keep the wire arms 2230, 2232 from tilting, each rack 2224, 2226 may be supported by a parallel guide shaft placed on the opposite side of the pinion gear 2229 that would slide with the rack 2224, 2226 when the parallel guide shaft is driven by the pinion gear 2229. In accordance with an alternative embodiment, (to the sliding support guide shafts), there may be another pinion gear stacked above or below the primary pinion gear described above. Two same-size pinion gears may be on each side of this secondary pinion gear and have a corresponding rack on each side of them. The ends of these racks are also connected to the wire arms 2230, 2232, and are configured to match the movement of the two primary racks 2224, 2226 described above to provide more drive force and stability to the wire arms 2230, 2232.

In accordance with an exemplary embodiment, the housing member 2210 can be, for example, approximately 20 mm to 40 mm by approximately 20 mm to 40 mm with the length of the wire arms 2230, 2232 being, for example, 5 mm to 20 mm in length measured from a lower surface 2212 of the housing member 2210.

In accordance with an exemplary embodiment, the skin-interface members 2240, 2242 can include, for example, a U-shape design 2240, 2242, (FIG. 23A), an inward facing semi-circular shape 2241, 2243 (FIG. 23B), a relatively straight surface 2244, 2246 (FIG. 23C), or an outward facing semi-circular shape 2245, 2247. In addition, the wire arms 2126, 2136 of the clip 2100 as shown in FIG. 22 can have similar shapes as those skin-interface members as shown in FIGS. 23A-23D.

Figure 24:
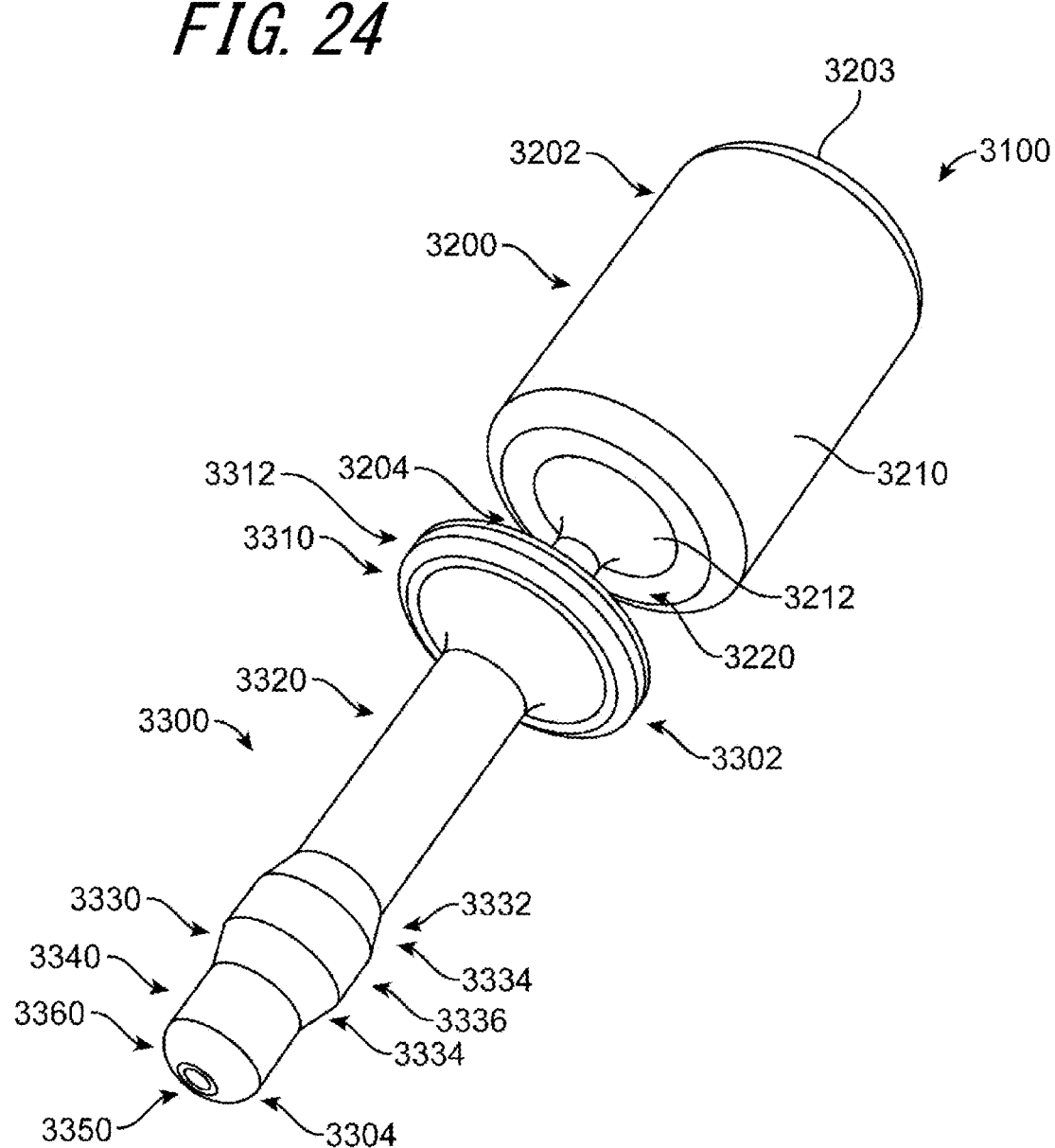
FIG. 24 is a perspective view of a subcutaneous plug assembly in accordance with an exemplary embodiment.
Figure 25:
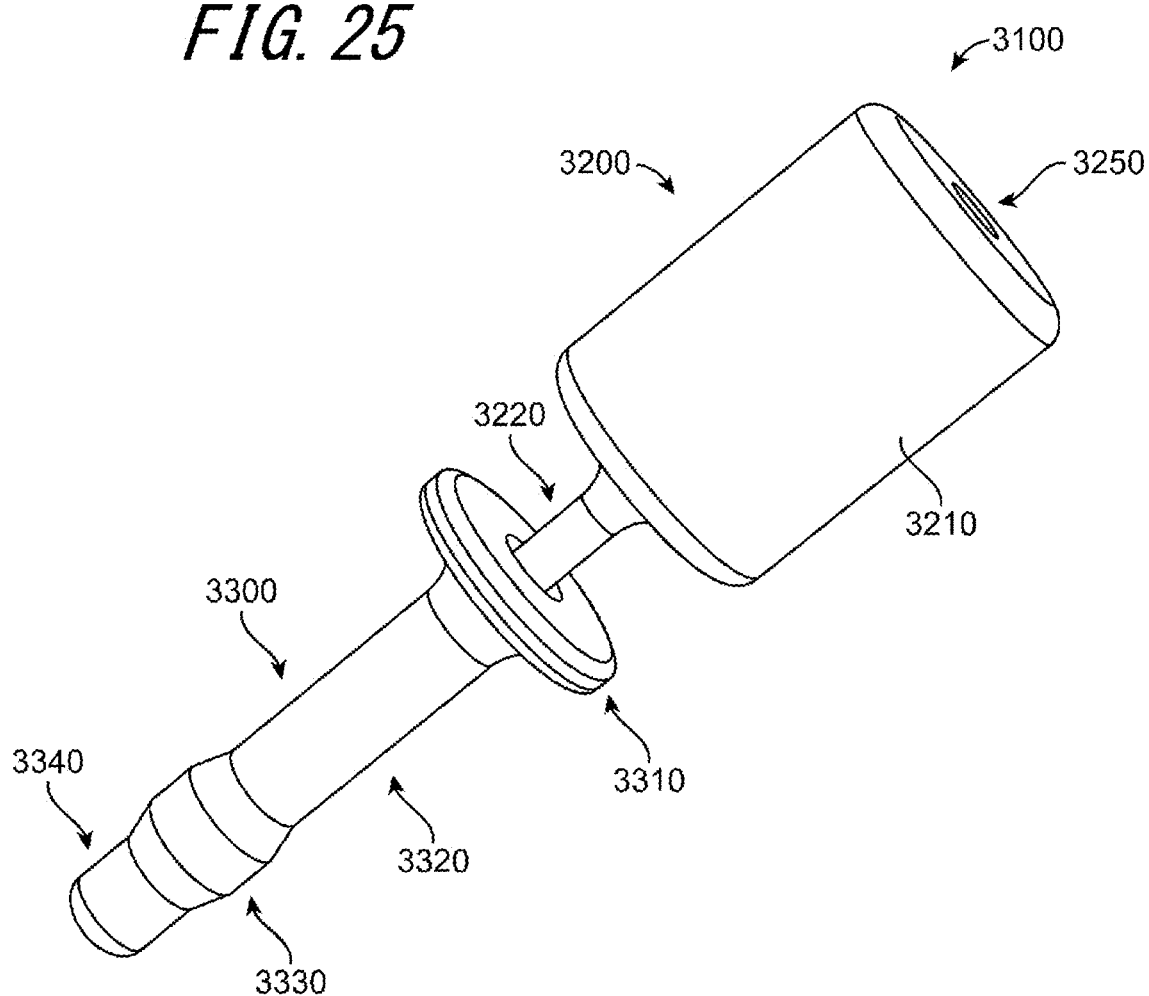
FIG. 25 is another perspective view of a subcutaneous plug assembly in accordance with an exemplary embodiment.

FIGS. 24 and 25 are perspective views of a subcutaneous plug assembly 3100 in accordance with an exemplary embodiment. As shown in FIG. 24, the subcutaneous plug assembly 3100 includes a pusher 3200 and a subcutaneous plug 3300. In accordance with an exemplary embodiment, the pusher 3200 can advance the subcutaneous plug 3300 over the guidewire 3400 (FIG. 26) into the wound channel. The pusher 3200 and the guidewire 3400 are removed and the subcutaneous plug 3300 can achieve hemostasis. Once hemostasis is achieved, the subcutaneous plug 3300 is removed. In accordance with an exemplary embodiment, the subcutaneous plug 3300 is of a length, which does not reach the blood vessel of the patient.

In accordance with an exemplary embodiment, the pusher 3200 is configured to push the subcutaneous plug 3300 over the guidewire 3400 to the wound site. For example, as shown in FIG. 24, the pusher 3200 can have a first cylindrical member 3210 on the proximal portion 3202 and a second cylindrical member 3220 on the distal portion 3204. In accordance with an exemplary embodiment, an outer diameter of the distal portion 3204 is smaller than an outer diameter of the proximal portion 3202. For example, the second cylindrical member 3220 is configured to fit within the subcutaneous plug 3300 and the first cylindrical member 3210 has a distal end 3212. The pusher 3200 includes a guidewire lumen 3250 configured to receive a guidewire 3400, which extends from a proximal end 3203 to a distal end 3205 (FIG. 29A) of the pusher 3200.

In accordance with an exemplary embodiment, the subcutaneous plug 3300 is preferably cylindrical in shape having a proximal portion 3310 on a proximal end 3302. In accordance with an exemplary embodiment, the proximal end 3302 of the subcutaneous plug 3300 can include a cylindrical plate 3312, which can help control a depth of insertion of the subcutaneous plug 3300. For example, in accordance with an exemplary embodiment, the cylindrical plate 3312 can help prevent the subcutaneous plug 3300 from penetrating too deep into the tissue. The subcutaneous plug 3300 also includes a middle portion 3320 extending between the proximal portion 3310 to an expanded portion 3330, and a distal portion 3340 extending from the expanded portion 3330 to the distal end 3304. In accordance with an exemplary embodiment, an outer diameter of the expanded portion 3330 is greater than an outer diameter of the proximal and the middle portions 3320, 3340. The expanded portion 3330 is configured to seal off the bleeding in the wound channel.

In accordance with an exemplary embodiment, the distal end 3304 of the subcutaneous plug has a self-closing hole 3350. The self-closing hole 3350 may be a small hole in a membrane at the distal end 3304 or a small axial hole in the center of a cylinder at the distal portion 3340. In either configuration, the hole 3350 is closed at its passive state by the elasticity of the material. The subcutaneous plug 3300 also includes a guidewire lumen 3360, which extends from the proximal end 3302 to the distal end 3304. In accordance with an exemplary embodiment, two or more subcutaneous plugs 3300 can be manufactured or mold together in a side-by-side manner for shipping and storage in an operating room or hospital.

Figure 26:
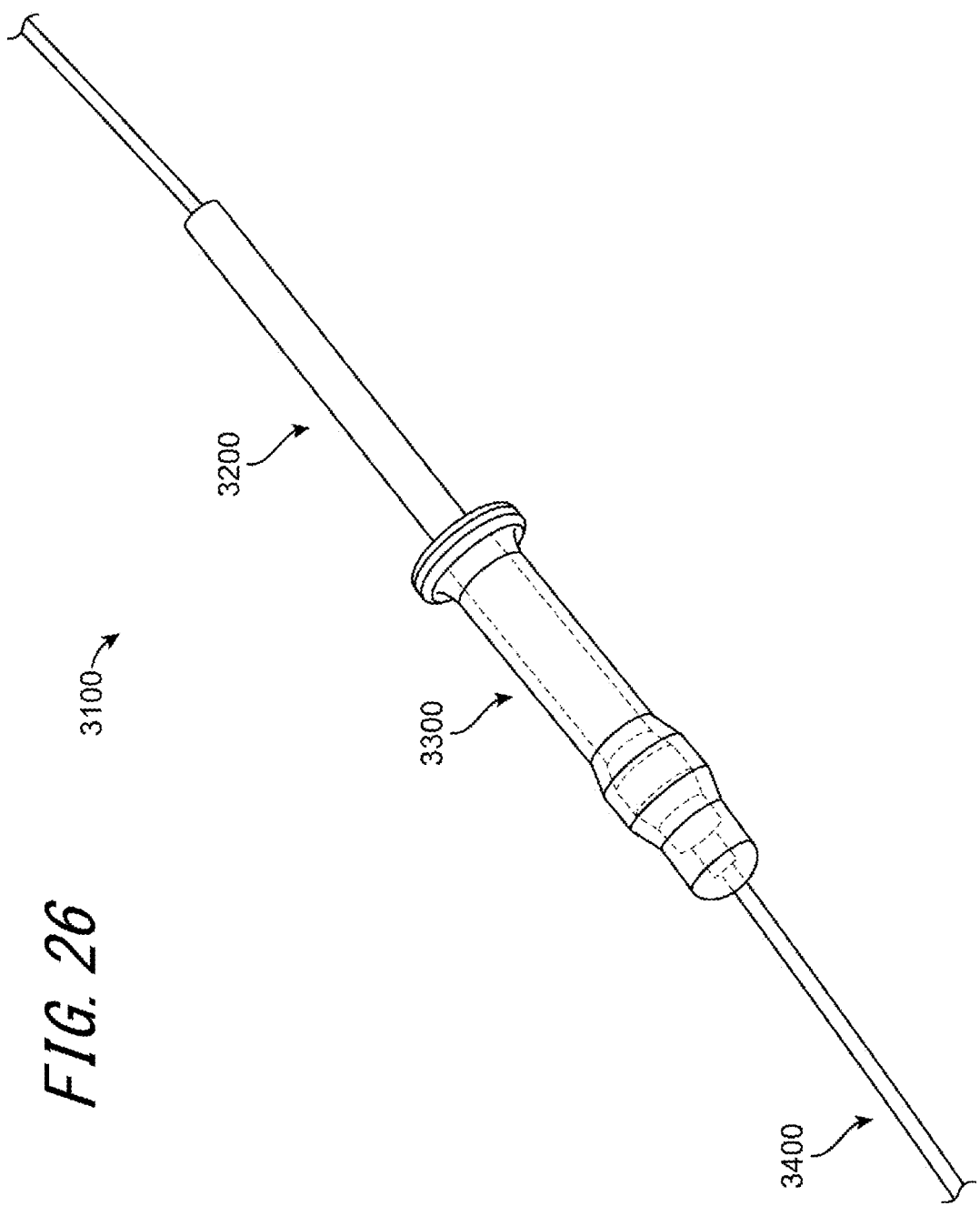
FIG. 26 is a perspective view of a subcutaneous plug assembly and a guidewire in accordance with an exemplary embodiment.

FIG. 26 is a perspective view of a subcutaneous plug assembly 3100 and a guidewire 3400 in accordance with an exemplary embodiment. As shown in FIG. 26, the subcutaneous plug 3300 is inserted over the guidewire 3400 and can be pushed by the pusher 3200 into the wound channel. Once the subcutaneous plug 3300 has been placed in the wound channel, the guidewire 3400 and the pusher (or pushing element) 3200 can be removed (as necessary).

Figure 27:
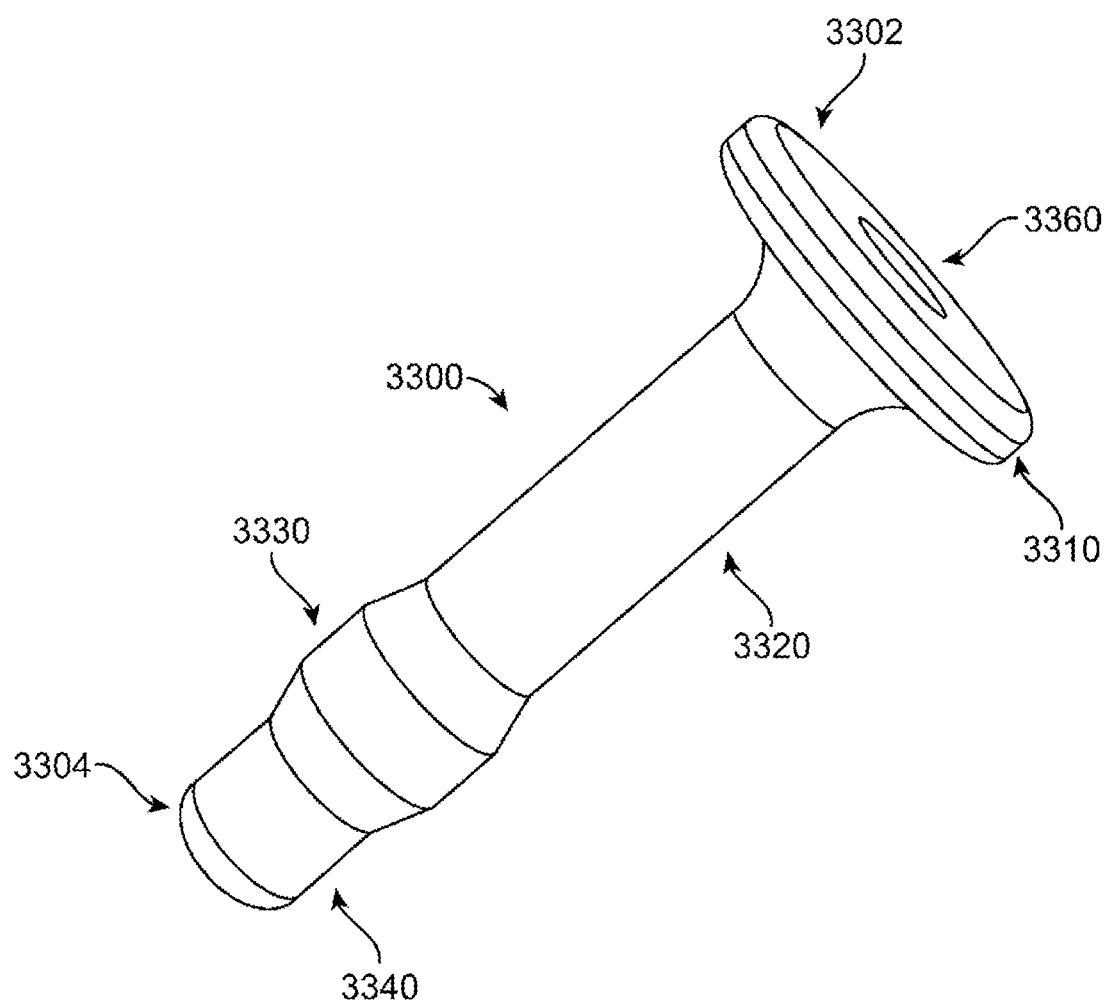
FIG. 27 is a perspective view of a subcutaneous plug assembly in accordance with an exemplary embodiment.

FIG. 27 is a perspective view of a subcutaneous plug 3300 in accordance with an exemplary embodiment. In accordance with an exemplary embodiment, the subcutaneous plug 3300 preferably has an overall length of 5 mm to 20 mm, and more preferably about 10 mm. In addition, the subcutaneous plug 3300 can have an outer diameter (or external diameter) in the middle portion 3320, the expanded portion 3330, and the distal portion 340 of approximately 2 mm to 7 mm.

In accordance with an exemplary embodiment, the subcutaneous plug 3300 is preferably a silicone material. In accordance with an exemplary embodiment, the subcutaneous plug 3300 can be made from an elastomer, a fluorocarbon, a rubber, or the like. In accordance with an exemplary embodiment, an outer diameter of the expanded portion 3330 is greater than an outer diameter of the proximal and the middle portions 3320, 3340. In accordance with an exemplary embodiment, the distal end 3304 of the subcutaneous plug has a self-closing hole 3350. The subcutaneous plug 3300 also includes a guidewire lumen 3360, which extends from the proximal end 3302 to the distal end 3304. In accordance with an exemplary embodiment, the proximal end 3302 of the guidewire lumen 3360 of the subcutaneous plug 3300 can also be configured to receive the second cylindrical member 3220 on the distal portion 3204 of the pusher 3200 to help place the subcutaneous plug 3300 within the wound channel.

FIG. 28 is a perspective view of a subcutaneous plug 3300 in accordance with another exemplary embodiment. In accordance with an exemplary embodiment, the subcutaneous plug 3300 as shown in FIG. 28 can include an inflate port 3500, which can inflate the expanded portion 3330 of the subcutaneous plug 3300. In accordance with an exemplary embodiment, the inflate port 3500 is arranged on the proximal portion 3310 of the subcutaneous plug 3300. For example, in accordance with an exemplary embodiment, the expanded portion 3330 can be inflated with a fluid or gas, for example, sterile water or saline.

Figure 29A:
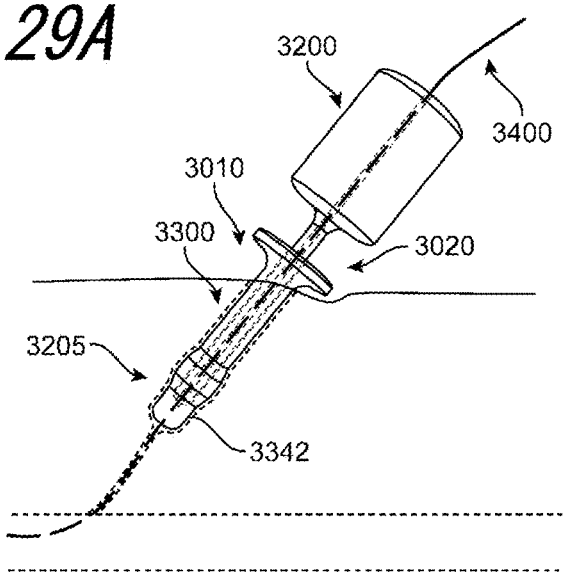
FIG. 29A is an illustration of placing the subcutaneous plug in an access site in accordance with an exemplary embodiment.
Figure 29B:
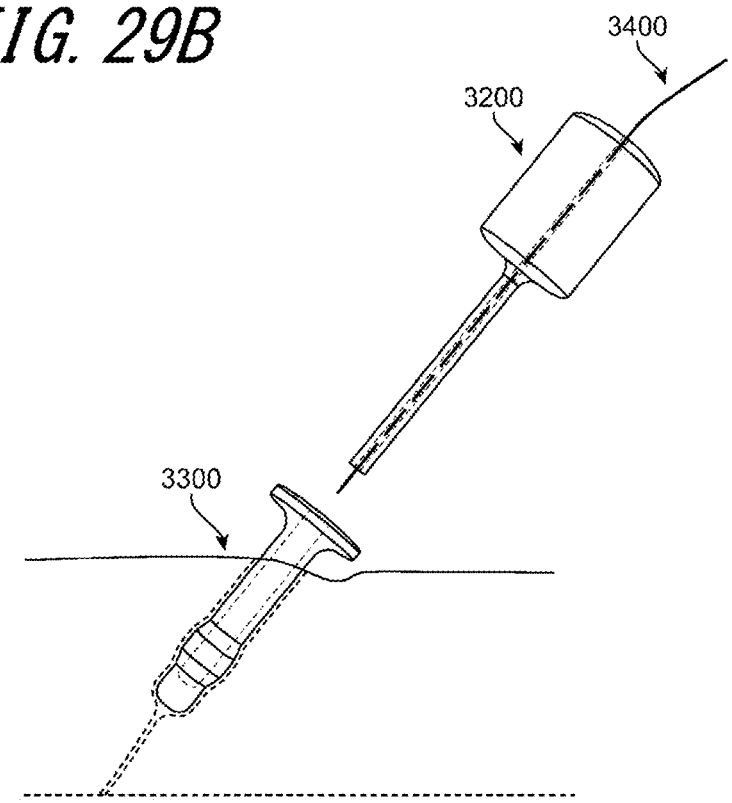
FIG. 29B is an illustration of placing the subcutaneous plug in an access site in accordance with an exemplary embodiment.

FIGS. 29A and 29B are illustrations of placing the subcutaneous plug 3300 in an access site (or wound site) 3010 in accordance with an exemplary embodiment. As shown in FIG. 29A, the pusher 3200 and the subcutaneous plug 3300 are advanced over a guidewire 3400 into a wound channel of the living body. Once in the access site 3010, the distal end 3205 of the pusher 3200 engages the inner surface 3342 of the distal portion 3340 of the subcutaneous plug 3300, which advances the subcutaneous plug 3300 into the access site 3010. In accordance with an exemplary embodiment, a length of the second cylindrical member 3220 of the pusher 3200 can be greater than, for example, the length of the subcutaneous plug 3300 such that during insertion of the subcutaneous plug 3300 into the access site 3010, a space 3020 is present in case the subcutaneous plug extends during insertion. As shown in FIG. 29B, once the subcutaneous plug 3300 has been inserted into the access site 3010, the guidewire 3200 and the pusher 3400 are removed.

The detailed description above describes embodiments of a medical device, and more particularly, a subcutaneous tissue device, subcutaneous plugs, and methods for achieving hemostasis with the subcutaneous tissue device and/or subcutaneous plugs. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

The invention claimed is:

1. A system for hemostasis in a living body, the system comprising:
    a medical device comprising:
        a base configured to be arranged on an upper surface of the tissue in the living body, the base including one or more openings extending inward from an outer edge of the base;
        a plurality of levers, each of the plurality of levers having a needle arranged on a lower surface of the plurality of levers and configured to puncture the tissue in the living body, and wherein the plurality of levers are configured to be received in a slot or track of the base; and
        at least one tie, the at least one tie configured to hold together the plurality levers and needles upon compressing the tissue in the living body upon moving the plurality of levers inward in the slot or track of the base; and at least one medical sheath or catheter configured to be arranged in the one or more openings of the base.

2. The system according to claim 1, wherein the plurality of levers are four, and the at least one tie is a pair of ties.

3. The system according to claim 1, further comprising:
a locking member, the locking member configured to secure the at least one tie.

4. The system according to claim 1, wherein each of the needles has a length of about 5 mm to 20 mm from the lower surface of the lever.

5. The system according to claim 1, wherein each of the plurality of needles has an angled tip, and wherein the angled tip points inward towards a center of the medical device.

6. The system according to claim 1, wherein the base is a rectangular plate, the one or more openings configured to receive the at least one medical sheath or catheter such that the at least one medical sheath or catheter can pass through the medical device and the medical device can be placed over an inserted sheath or catheter.

7. The system according to claim 1, wherein the at least one tie is a single loop tie.

8. The system according to claim 1, wherein the slot or track of the base is arranged on a lower surface of the base and the plurality of levers disengage from the base upon reaching a center of the base.

9. The system according to claim 8, wherein at least a portion of the base disengages with the plurality of levers upon reaching the center of the base.

10. The system according to claim 8, wherein the one or more openings extending inward from the outer edge of the base are wedge shaped.

11. A method of achieving hemostasis with the system according to claim 1, the method comprising:
puncturing the tissue in the living body with the plurality of needles of the medical device;
compressing the tissue in the living body by gathering the plurality of needles; and
locking the plurality of needles together.

12. The method according to claim 11, wherein each of the plurality of needles are L-shaped needles.

13. The method according to claim 11, comprising:
removing the base after compressing the tissue in the living body by gathering the plurality of needles or locking the plurality of needles together.

14. A system for hemostasis in a living body, the system comprising:
a medical device comprising:
a rectangular base configured to be arranged on an upper surface of the tissue in the living body, the rectangular base including a pair of wedge shaped openings extending inward from an outer edge of the rectangular base;
a plurality of levers, each of the plurality of levers having a needle arranged on a lower surface of the plurality of levers and configured to puncture the tissue in the living body, and wherein the plurality of levers are configured to be received in a slot or track of the rectangular base; and at least one tie, the at least one tie configured to hold together the plurality levers and needles upon compressing the tissue in the living body upon moving the plurality of levers inward in the slot or track of the rectangular base; and at least one medical sheath or catheter configured to be arranged in the one or more openings of the rectangular base.

15. The system according to claim 14, wherein the plurality of levers are four, and the at least one tie is a pair of ties.

16. The system according to claim 14, further comprising:
a locking member, the locking member configured to secure the at least one tie.

17. The system according to claim 14, wherein each of the needles has a length of about 5 mm to 20 mm from the lower surface of the lever.

18. The system according to claim 14, wherein each of the plurality of needles has an angled tip, and wherein the angled tip points inward towards a center of the medical device.

19. The system according to claim 14, wherein the at least one tie is a single loop tie.

20. The system according to claim 14, wherein the slot or track of the rectangular base is arranged on a lower surface of the rectangular base and the plurality of levers disengage from the rectangular base upon reaching a center of the rectangular base.

21. The system according to claim 20, wherein at least a portion of the rectangular base disengages with the plurality of levers upon reaching the center of the rectangular base.

22. A system for hemostasis in a living body, the system comprising:
a medical device comprising:
a rectangular base configured to be arranged on an upper surface of the tissue in the living body, the rectangular base including one or more wedge shaped openings extending inward from an outer edge of the rectangular base;
a plurality of levers, each of the plurality of levers having a needle arranged on a lower surface of the plurality of levers and configured to puncture the tissue in the living body, and wherein the plurality of levers are configured to be received in a slot or track of the rectangular base; and
at least one tie, the at least one tie configured to hold together the plurality levers and needles upon compressing the tissue in the living body upon moving the plurality of levers inward in the slot or track of the rectangular base; and
at least one medical sheath or catheter configured to be arranged in the one or more wedge shaped openings of the rectangular base.

* * * * *